United States Patent
Weiner et al.

(10) Patent No.: US 10,301,617 B2
(45) Date of Patent: May 28, 2019

(54) METHODS FOR THE PRODUCTION OF LIBRARIES FOR DIRECTED EVOLUTION

(71) Applicant: AxioMx, Inc., Branford, CT (US)

(72) Inventors: Michael Weiner, Guilford, CT (US); Margaret Kiss, Westbrook, CT (US)

(73) Assignee: AxioMx, Inc., Branford, CT (US)

( * ) Notice: Subject to any disclaimer, the term of this patent is extended or adjusted under 35 U.S.C. 154(b) by 229 days.

(21) Appl. No.: 15/476,304

(22) Filed: Mar. 31, 2017

(65) Prior Publication Data
US 2017/0204404 A1     Jul. 20, 2017

Related U.S. Application Data

(60) Division of application No. 15/199,120, filed on Jun. 30, 2016, now Pat. No. 9,617,537, which is a
(Continued)

(51) Int. Cl.
*C40B 50/06* (2006.01)
*C12N 15/10* (2006.01)
(Continued)

(52) U.S. Cl.
CPC .......... *C12N 15/1058* (2013.01); *C07K 16/00* (2013.01); *C12N 15/1024* (2013.01); *C12N 15/1037* (2013.01); *C12N 15/1068* (2013.01); *C12N 15/1093* (2013.01); *C12N 15/907* (2013.01); *C07K 2317/14* (2013.01); *C07K 2317/51* (2013.01); *C07K 2317/515* (2013.01); *C07K 2317/622* (2013.01); *C40B 30/04* (2013.01); *C40B 50/06* (2013.01)

(58) Field of Classification Search
None
See application file for complete search history.

(56) References Cited

U.S. PATENT DOCUMENTS

| 6,803,216 B2 | 10/2004 | Hogrefe et al. |
| 2013/0045507 A1 | 2/2013 | Huovinen et al. |

FOREIGN PATENT DOCUMENTS

| CN | 1210557 A | 3/1999 |
| WO | WO-2014/100419 A1 | 6/2014 |
| WO | WO-2015/085079 A2 | 6/2015 |

OTHER PUBLICATIONS

First Office Action for Chinese Patent Application No. 201480023547. 1, dated Mar. 2, 2017 (25 pages).
(Continued)

*Primary Examiner* — Christian C Boesen
(74) *Attorney, Agent, or Firm* — Clark & Elbing LLP

(57) ABSTRACT

Disclosed herein is an efficient method of generating a library of variants of a sequence of interest, such as may be used in directed evolution, in one embodiment, the method includes an amplification reaction, e.g. error-prone PCR, to generate double-stranded DNA (dsDNA) variants of a sequence of interest, after which one strand of the dsDNA variants may be selectively degraded to produce single-stranded DNA (ssDNA) variants. The ssDNA variants may be hybridized to ssDNA intermediaries, e.g., uracilated circular ssDNA intermediaries, to form heteroduplex DNA, which may be transformed into cells, such as *E. coli* cells, yielding a library of variants. This method eliminates the inefficient sub-cloning steps and the need for costly primer sets required by many prior methods.

7 Claims, 8 Drawing Sheets

Specification includes a Sequence Listing.

Related U.S. Application Data continuation of application No. 14/770,355, filed as application No. PCT/US2014/018672 on Feb. 26, 2014, now Pat. No. 9,422,549.

(60) Provisional application No. 61/769,517, filed on Feb. 26, 2013.

(51) Int. Cl.
    *C07K 16/00*     (2006.01)
    *C12N 15/90*     (2006.01)
    *C40B 30/04*     (2006.01)

(56) References Cited

OTHER PUBLICATIONS

Supplementary European Search Report for European Application No. 14757218.4, dated Jan. 30, 2017 (8 pages).
"Site-Directed Mutagenesis—Kunkel Method," <http://www.bio.davidson.edu/molecular/kunkel/kunkel.html>, retrieved on Oct. 30, 2015 (4 pages).
Holland et al., "AXM mutagenesis: an efficient means for the production of libraries for directed evolution of proteins," J Immunol Methods. 394(1-2):55-61 (2013).
Huovinen et al., "Primer extension mutagenesis powered by selective rolling circle amplification," PLoS One. 7(2):e31817 (2012) (9 pages).
Neylon, "Chemical and biochemical strategies for the randomization of protein encoding DNA sequences: library construction methods for directed evolution," Nucleic Acids Res. 32(4):1448-59 (2004).
Nikiforov et al., "The use of phosphorothioate primers and exonuclease hydrolysis for the preparation of single-stranded PCR products and their detection by solid-phase hybridization," PCR Methods Appl. 3(5):285-91 (1994).
Pertzev et al., "Eco29kl, a novel plasmid encoded restriction endonuclease from *Escherichia coli*," Nucleic Acids Res. 20(8):1991 (1992).
Rasila et al., "Critical evaluation of random mutagenesis by error-prone polymerase chain reaction protocols, *Escherichia coli* mutator strain, and hydroxylamine treatment," Anal Biochem. 388(1):71-80 (2009).
Sayers et al., "5'-3' exonucleases in phosphorothioate-based oligonucleotide-directed mutagenesis," Nucleic Acids Res. 16(3):791-802 (1988).
Volkov et al., "Recombination and chimeragenesis by in vitro heteroduplex formation and in vivo repair," Nucleic Acids Res. 27(18):e18 (1999) (6 pages).
International Preliminary Report on Patentability for International Patent Application No. PCT/US14/18672, dated Sep. 1, 2015 (9 pages).
International Search Report and Written Opinion for International Patent Application No. PCT/US14/18672, dated Aug. 11, 2014 (19 pages).
Supplementary Partial European Search Report for European Application No. 14757218.4, dated Oct. 24, 2016 (6 pages).
Communication pursuant to Article 94(3) EPC for European Application No. 14757218.4, dated Jul. 30, 2018 (6 pages).
Examination Report No. 1 for Australian Patent Application No. 2014223602, dated Aug. 4, 2017 (4 pages).
Lim et al., "Directed evolution of nucleotide-based libraries using lambda exonuclease," Biotechniques 53(6):357-64 (2012).
Notice of Reasons for Rejection for Japanese Patent Application No. 2015-559299, dated Jan. 16, 2018 (9 pages).

1-Obtention of VH and VL sequences

2-Cloning into pFUSE-CHIg and pFUSE2-CLIg

METHODS FOR THE PRODUCTION OF LIBRARIES FOR DIRECTED EVOLUTION

CROSS-REFERENCE TO RELATED APPLICATION

This application claims benefit of priority to U.S. Provisional Application No. 61/769,517, filed Feb. 26, 2013, which is hereby incorporated by reference.

BACKGROUND OF THE INVENTION

In general, the present invention relates to improved nucleic acid library production.

Libraries of diverse genetic sequences may be useful in identifying proteins with a specific function. For example, commercially valuable functional sequences may be identified by expressing a library of diverse genetic sequences, testing the resultant proteins for a specific function, and isolating those sequences that perform well. This process may be referred to as directed evolution. Sequences may be further optimized for a particular function by repetitive cycles of diversification and selection. Sequences selected from diverse sequence pools may be useful in biological, medical, or industrial applications. For example, a sequence identified by directed evolution may be used in antibody engineering.

Prior methods of generating libraries of diverse genetic sequences are often inefficient. For instance, prior methods may include an inefficient ligation step or require costly primer sets. Improving upon the speed and cost-effectiveness of known methods will increase the efficiency of library generation, enable high-throughput parallel processing of multiple functional sequences, and promote the identification of new functional sequences.

SUMMARY OF THE INVENTION

The present invention includes a method of generating a library of variants of a sequence of interest. The method may include the steps of first providing a template DNA molecule including the sequence of interest and providing a pair of oligonucleotides in which one of the oligonucleotides may be protected and the other oligonucleotide may be non-protected, and in which the oligonucleotides hybridize to opposite strands of the sequence of interest and flank the sequence of interest. A subsequent step may include performing an amplification reaction on the template DNA molecule using the oligonucleotides, thereby generating a population of dsDNA variants, followed by the step of incubating the population of dsDNA variants with an enzyme capable of selectively degrading the non-protected strand over the protected strand of the dsDNA variants, thereby producing a population of ssDNA variants. Next, the population of ssDNA variants may be hybridized to ssDNA intermediaries, which may include a sequence substantially identical to the sequence of interest or a fragment thereof, generating heteroduplex DNA. Following the generation of heteroduplex DNA, a subsequent step may include transforming the heteroduplex DNA into cells, thereby generating a library of variants of the sequence of interest.

The template DNA molecule may be a linear dsDNA molecule, a circular dsDNA molecule, a circular ssDNA molecule, an uracilated circular ssDNA molecule, or a methylated circular ssDNA molecule. The sequence of the template DNA molecule may be substantially identical to the sequence of the ssDNA intermediaries.

The sequence of interest may be greater than 100 basepairs, greater than 300, greater than 500, or greater than 700 basepairs. The sequence of interest may be between 100 and 2000 basepairs, between 300 and 1500 basepairs, or between 700 and 1200 basepairs.

In some embodiments, the protected oligonucleotide may be an oligonucleotide that includes three or more 5' phosphorothioates. The protected oligonucleotide may include three, four, or five 5' phosphorothioates. The non-protected oligonucleotide may be an oligonucleotide that does not include three or more 5' phosphorothioates. In some embodiments, the enzyme capable of selectively degrading the non-protected strand over the protected strand may be T7 exonuclease or lambda exonuclease. In other embodiments, the protected oligonucleotide may be an oligonucleotide that includes a 5' phosphate and the non-protected oligonucleotide may be an oligonucleotide that does not include a 5' phosphate. In such embodiments, the enzyme capable of selectively degrading the non-protected strand over the protected strand may be lambda exonuclease.

In various embodiments, the amplification reaction may be a PCR reaction, an error-prone PCR reaction, an isothermal amplification reaction, or a rolling circle amplification reaction. In some embodiments, 50% of dsDNA variants of the population of dsDNA variants have less than 99.5% identity with the sequence of interest or less than 98% identity with the sequence of interest.

Any of the above embodiments may further include purifying the population of dsDNA variants prior to incubation with the enzyme capable of selectively degrading the non-protected strand over the protected strand. Any of the above embodiments may further include purifying the population of ssDNA variants prior to hybridization to the ssDNA intermediaries.

In any of the above embodiments, the ssDNA intermediaries may include a sequence with at least 50%, at least 70%, at least 90%, or 100% identity to the sequence of interest or to a fragment thereof. The ssDNA intermediaries may be phagemids or vectors including sequence fragments substantially identical to the sequence of a phagemid.

In any of the above embodiments, the hybridizing of the population of ssDNA variants to the ssDNA intermediaries may include co-incubation of the population of ssDNA variants and the ssDNA intermediaries at a denaturing temperature followed by gradual cooling to an annealing temperature. The denaturing temperature may be about 90° C. The annealing temperature may be about 55° C. The gradual cooling occurs at a rate of about −1° C. per minute.

The cells of the present invention may be eukaryotic cells, mammalian cells, insect cells, yeast cells, or bacterial cells.

In any of the above embodiments, the ssDNA intermediaries may include modified nucleobases or nucleobases other than adenine, guanine, cytosine, and thymine. The cells may be capable of selectively degrading the ssDNA intermediaries. In some particular embodiments, the ssDNA intermediaries may be uracilated ssDNA intermediaries. In other particular embodiments, the ssDNA intermediaries may be methylated ssDNA intermediaries. In certain embodiments, the cells capable of selectively degrading the ssDNA intermediaries may be Ung+ bacterial cells or TG1 E. coli cells. In other embodiments, the cells capable of selectively degrading the ssDNA intermediaries may be Mcr+ bacterial cells.

Further embodiments may include extending the ssDNA variants hybridized to the ssDNA intermediaries by incubation of the heteroduplex DNA with DNA polymerase. The incubation of the heteroduplex DNA with DNA polymerase may include incubation of the heteroduplex DNA with a DNA polymerase and a DNA ligase. The ssDNA intermediaries may be methylated ssDNA intermediaries and the method may further include the steps of denaturing the heteroduplex DNA and incubating the denatured product with an enzyme that selectively degrades methylated DNA. In particular embodiments, the methylated ssDNA intermediaries may include methylated adenine nucleobases, and the enzyme that selectively degrades methylated DNA may be DpnI. In some embodiments, the ssDNA variants may be methylated and the ssDNA intermediaries may not be methylated, and the method further includes the steps of denaturing the heteroduplex DNA and incubating the denatured product with an enzyme that selectively degrades non-methylated DNA. In particular embodiments, the methylated ssDNA variants include methylated cytosine or guanine nucleobases, and such that the enzyme that selectively degrades non-methylated DNA may be Sau3AI or a restriction enzyme that recognizes the DNA sequence 5'-GATC-3'.

In any of the above embodiments, the method may further include purifying the heteroduplex DNA prior to transformation into the cells. The transforming of the heteroduplex DNA into the cells may include the independent transformation of two or more, 10 or more, 20 or more, or 50 or more aliquots of the cells. One or more aliquots of the library of variants may be cultured to generate a cultured library. The aliquots may be cultured in a recovery media. The one or more aliquots of the library of variants may be cultured independently or combined in a single culture. The cultured library may be pelleted to generate a pelleted cultured library. The pelleted cultured library may be stored at a temperature of −20° C. or less. The pelleted cultured library may be resuspended to generate a resuspended pelleted cultured library. The resuspended pelleted cultured library may be stored at a temperature of −20° C. or less. One or more aliquots of the cultured library may be incubated with a helper phage, generating a phage display library. The one or more aliquots of the cultured library may be incubated with the helper phage independently or may be combined for incubation with the helper phage. The phage display library may be pelleted to generate a pelleted phage display library. The pelleted phage display library may be stored at a temperature of −20° C. or less. The pelleted phage display library may be resuspended to generate a resuspended pelleted phage display library. The resuspended pelleted phage display library may be stored at a temperature of −20° C. or less. The cultured library may be diluted or serially diluted to generate a diluted or serially diluted cultured library. The diluted or serially diluted cultured library may be plated to culture plates, such that the culture plates may be incubated at a temperature conducive to growth or division of cells.

In any of the above embodiments, the sequence of interest may encode an antibody or a domain or fragment thereof, a polymerase or a domain or fragment thereof, an enzyme or a domain or fragment thereof, a single-chain variable fragment antibody or a domain or fragment thereof, a kinase or a domain or fragment thereof, a DNA binding protein or a domain or fragment thereof, an RNA binding protein or a domain or fragment thereof, a transcription factor or a domain or fragment thereof, or a human protein or a domain or fragment thereof. The sequence of interest or the sequence of the ssDNA intermediaries may include a bacteriophage coat protein.

In some embodiments, at least 30%, at least 50%, or at least 70% of the transformed cells may include a variant of the sequence of interest.

In any of the above embodiments, the steps of providing a template DNA molecule including the sequence of interest, providing a pair of oligonucleotides, performing an amplification reaction on the template DNA molecule using the oligonucleotides, and incubating the resultant population of dsDNA variants with an enzyme capable of selectively degrading the non-protected strand over the protected strand of the dsDNA variants may be performed in parallel from each of two or more different sequences of interest to produce two or more populations of ssDNA variants, such that the oligonucleotides, the amplification reaction, and the enzyme may differ in the application of any or all of the steps to each of the two or more different sequences of interest. The populations of ssDNA variants may be admixed prior to or during subsequent hybridization to ssDNA intermediaries. In some embodiments, at least two of the two or more different sequences of interest may be amplified from a single template DNA molecule. In certain embodiments, all of the two or more different sequences of interest may be amplified from a single template DNA molecule. In some embodiments, at least two of the two or more different sequences of interest may be amplified from different template DNA molecules. In certain embodiments, each of the two or more different sequences of interest may be amplified from a different template DNA molecule. In still other embodiments, one or more of the steps performed in parallel may be performed in a single reaction for at least two of the two or more different sequences of interest. In some embodiments, one or more of the steps performed in parallel may be performed in a single reaction for all of the two or more different sequences of interest. In some embodiments, One or more of the steps performed in parallel may be carried out separately for at least two of the two or more different sequences of interest or for each of the two or more different sequences of interest. In particular embodiments, the ssDNA intermediaries may include a sequence substantially identical to each of the two or more different sequences of interest, or fragments thereof, such that hybridization encompasses the hybridization of each of the two or more populations of ssDNA variants to the ssDNA intermediaries. In certain embodiments, two or more populations of ssDNA variants may be hybridized to the ssDNA intermediaries simultaneously or sequentially.

A method of generating a population of dsDNA variants by error-prone PCR may include the steps of providing a template DNA molecule including the sequence of interest, providing a pair of oligonucleotides such that the oligonucleotides hybridize to opposite strands of the sequence of interest, such that one of the oligonucleotides includes three or more 5' phosphorothioates and the other oligonucleotide does not include three or more 5' phosphorothioates, and the oligonucleotides flank the sequence of interest, and performing error-prone PCR on the template DNA molecule using the oligonucleotides, thereby generating a population of dsDNA variants.

A method of generating a population of ssDNA variants by error-prone PCR may include the steps of providing a template DNA molecule including the sequence of interest, providing a pair of oligonucleotides such that the oligonucleotides hybridize to opposite strands of the sequence of interest, such that one of the oligonucleotides includes three or more 5' phosphorothioates and the other oligonucleotide does not include three or more 5' phosphorothioates, and the oligonucleotides flank the sequence of interest, performing error-prone PCR on the template DNA molecule using the oligonucleotides, thereby generating a population of dsDNA variants, and incubating the population of dsDNA variants with an enzyme capable of hydrolyzing the non-phosphorothioate strand but not the phosphorothioate strand of the dsDNA variants, thereby producing a population of ssDNA variants.

A method of generating a population of dsDNA molecules by PCR may include the steps of providing a template DNA molecule including the sequence of interest, providing a pair of oligonucleotides such that the oligonucleotides hybridize to opposite strands of the sequence of interest, such that one of the oligonucleotides includes three or more 5' phosphorothioates and the other oligonucleotide does not include three or more 5' phosphorothioates, and the oligonucleotides flank the sequence of interest, and performing PCR on the template DNA molecule using the oligonucleotides, thereby generating a population of dsDNA molecules.

A method of generating a population of ssDNA molecules by PCR may include the steps of providing a template DNA molecule including the sequence of interest, providing a pair of oligonucleotides such that the oligonucleotides hybridize to opposite strands of the sequence of interest, such that one of the oligonucleotides includes three or more 5' phosphorothioates and the other oligonucleotide does not include three or more 5' phosphorothioates, and the oligonucleotides flank the sequence of interest, performing PCR on the template DNA molecule using the oligonucleotides, thereby generating a population of dsDNA molecules, and incubating the population of dsDNA molecules with an enzyme capable of hydrolyzing the non-phosphorothioate strand but not the phosphorothioate strand of the dsDNA molecules, thereby producing a population of ssDNA molecules.

A method of phage display may include the steps of providing a library of variants generated by an embodiment of the present invention, culturing one or more aliquots of the library of variants to generate a cultured library of variants, incubating one or more aliquots of the cultured library of variants with a helper phage to generate a phage display library, such that cells of the phage display library display variants of the protein encoded by the sequence of interest, contacting the cells of the phage display library to a target molecule, such that one or more of the variants of the protein encoded by the sequence of interest may interact with the target molecule, and isolating from amongst the cells of the phage display library those which display a variant protein that interacts with the target molecule. The variant protein may interact with the target molecule by binding the target molecule, cleaving the target molecule, catalyzing a reaction of the target molecule, inducing a conformational change in the target molecule, or modifying the target molecule. The target molecule may be a small molecule, a protein or a domain or fragment thereof, a pathogen protein or a domain or fragment thereof, an enzyme or a domain or fragment thereof, or a human protein or a domain or fragment thereof.

A method of selectively degrading a non-recombinant nucleic acid can include the steps of providing a first nucleic acid including at least one segment having a restriction site; providing a second nucleic acid including at least one segment that does not include the restriction site; subjecting the first nucleic acid and the second nucleic acid to a reaction for recombining the first nucleic acid and the second nucleic acid such that the segment of the first nucleic acid is replaced with the segment of the second nucleic acid, thereby generating a recombinant product that does not include the restriction site; transforming the product of the reaction into a cell expressing a restriction enzyme capable of cleaving the restriction site; and incubating the cell in a manner sufficient to allow cleavage by the restriction enzyme expressed by the cell. The method may further include the step of determining whether the cell includes a recombinant product that does not include a restriction site cleaved by the restriction enzyme and/or the step of isolating the recombinant product from the cell. The restriction enzyme can be Eco29kI. In any of these methods, the recombinant product can encode an immunoglobulin light chain and/or an immunoglobulin heavy chain, one or more of the immunoglobulin light chain and/or the immunoglobulin heavy chain encoded by at least a portion of the first nucleic acid and at least a portion of the second nucleic acid.

A method of selectively degrading a non-mutagenized nucleic acid can include the steps of providing a first nucleic acid including at least one segment having a restriction site; providing a second nucleic acid having at least one segment that does not include the restriction site and is capable of hybridizing to at least a segment of the first nucleic acid having the restriction site; hybridizing the second nucleic acid to the first nucleic acid, generating heteroduplex DNA; resolving the heteroduplex DNA, thereby generating a product that does not include the restriction site; transforming the product of the reaction into a cell expressing a restriction enzyme capable of cleaving the restriction site; and incubating the cell in a manner sufficient to allow cleavage by the restriction enzyme expressed by the cell. The method may further include the step of determining whether the cell includes a product that does not include a restriction site cleaved by the restriction enzyme and/or the step of isolating the products from the cell. The restriction enzyme can be Eco29kI. In any of these methods, the product can encode an immunoglobulin light chain and/or an immunoglobulin heavy chain, one or more of the immunoglobulin light chain and/or the immunoglobulin heavy chain encoded by at least a portion of the second nucleic acid or a sequence thereof. In any of these methods, the first nucleic acid can be an ssDNA intermediary and the second nucleic acid can be an ssDNA variant.

A method of selectively expressing a protein from a mutagenized open reading frame can include the steps of providing a first nucleic acid including one or more stop codons in at least one segment of an open reading frame otherwise capable of expression; providing a second nucleic acid including at least one segment that does not include a stop codon; subjecting the first nucleic acid and the second nucleic acid to a reaction for recombining the first nucleic acid and the second nucleic acid such that the segment of the first nucleic acid is replaced with the segment of the second nucleic acid, thereby generating a recombinant product that does not include a stop codon in the open reading frame; transforming the product of the reaction into a cell; and incubating the cell for period sufficient to allow expression of the open reading frame. The method can further include the step of determining whether the cell includes a protein or portion thereof expressed from an open reading frame including the sequence of a portion of the first nucleic acid and the sequence of at least a portion of the second nucleic acid and/or the step of isolating from the cell a protein or fragment thereof expressed from an open reading frame including the sequence of a portion of the first nucleic acid and the sequence of at least a portion of the second nucleic acid. In any of these methods, the recombinant product can encode an immunoglobulin light chain and/or an immunoglobulin heavy chain, one or more of the immunoglobulin light chain and/or the immunoglobulin heavy chain encoded by at least a portion of the first nucleic acid and at least a portion of the second nucleic acid. In any of these methods, the recombination reaction can be a mutagenesis reaction in which the first nucleic acid is an ssDNA intermediary and the second nucleic acid is an ssDNA variant.

A method of selectively expressing a protein from a mutagenized open reading frame can include the steps of providing a first nucleic acid including one or more stop codons in at least one segment of an open reading frame otherwise capable of expression; providing a second nucleic acid including at least one segment that does not include a stop codon and is capable of hybridizing to at least a segment of the first nucleic acid having one or more of the stop codons; hybridizing the second nucleic acid to the first nucleic acid, generating heteroduplex DNA; resolving the heteroduplex DNA, thereby generating a product that does not include a stop codon in the open reading frame, transforming the product of the reaction into a cell; and incubating the cell for period sufficient to allow expression of the open reading frame. The method can further include the step of determining whether the cell includes a protein or portion thereof expressed from an open reading frame including the sequence of a portion of the first nucleic acid and the sequence of at least a portion of the second nucleic acid and/or the step of isolating from the cell a protein or fragment thereof expressed from an open reading frame including the sequence of a portion of the first nucleic acid and the sequence of at least a portion of the second nucleic acid. In any of these methods, the product can encode an immunoglobulin light chain and/or an immunoglobulin heavy chain, one or more of the immunoglobulin light chain and/or the immunoglobulin heavy chain encoded by at least a portion of the second nucleic acid or a sequence thereof. In any of these methods, the recombination reaction can be a mutagenesis reaction in which the first nucleic acid is an ssDNA intermediary and the second nucleic acid is an ssDNA variant. Compositions may be produced by the methods of the present invention. These include a population of dsDNA variants, a population of ssDNA variants, a library of variants, a cultured library, a pelleted cultured library, a phage display library, a pelleted phage display library, a diluted cultured library, a serially diluted cultured library, and a plated serially diluted cultured library.

As used herein, the term "about" means+/−10% of the recited value.

By "substantially identical" is meant a nucleic acid having at least 35%, 40%, 50%, 55%, 60%, 65%, 70%, 75%, 85%, 90%, 95%, or even 99% identity as compared to a reference nucleic acid sequence. Sequence identity is typically measured using sequence analysis software with the default parameters specified therein (Sequence Analysis Software Package of the Genetics Computer Group, University of Wisconsin Biotechnology Center, 1710 University Avenue, Madison, Wis. 53705). This software program matches similar sequences by assigning degrees of homology to various substitutions, deletions, and other modifications. The length of comparison sequences will generally be at least 20 nucleotides (e.g., 60 nucleotides), preferably at least 90 nucleotides, and more preferably at least 120 nucleotides, or full length. It is to be understood herein that gaps may be found between the nucleobases of sequences that are identical or similar to nucleobases of the original sequence. The gaps may include no nucleobases or one or more nucleobases that are not identical or similar to the original nucleic acid.

Another indication that nucleotide sequences are substantially identical is if two molecules hybridize to each other under stringent conditions. Stringent conditions are sequence-dependent and will be different in different circumstances. Generally, stringent conditions are selected to be about 5° C. to about 20° C., usually about 10° C. to about 15° C., lower than the thermal melting point ($T_m$) for the specific sequence at a defined ionic strength and pH. The $T_m$ is the temperature (under defined ionic strength and pH) at which 50% of the target sequence hybridizes to a matched probe. Typically, stringent conditions will be those in which the salt concentration is about 0.02 molar at pH 7 and the temperature is at least about 60° C. For instance, in a standard Southern hybridization procedure, stringent conditions will include an initial wash in 6×SSC at 42° C. followed by one or more additional washes in 0.2×SSC at a temperature of at least about 55° C., typically about 60° C. and often about 65° C.

A DNA "sequence" means a series of nucleobases in a DNA molecule. The DNA molecule may be single stranded (ss) or double stranded (ds). When referring to the sequence of a dsDNA molecule, the term may refer to the sequence of either or both of the two strands of the dsDNA molecule. When referring to the sequence of a ssDNA molecule, the term may refer to the sequence of the ssDNA molecule, the sequence of a strand complementary to the ssDNA molecule, or both.

"Sequence of interest" means a series of nucleobases in a DNA molecule that may be used as a starting point in generating a library of variants.

A "fragment" of DNA is a sequence that includes at least about 10 consecutive nucleobases, such as about 10, 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1000, 1500, 2000, 2500, 3000, 3500 or 4000 nucleobases. A "fragment" of a protein means a series of at least 6 amino acids, such as about 6, 8, 10, 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1000, or more amino acids.

A "variant of a sequence of interest" means a sequence derived from a sequence of interest, such as a sequence derived from a sequence of interest through an amplification reaction, that contains one or more sequence changes as compared to the sequence of interest. A variant of a sequence of interest may have 70%-99.9% identity with said sequence of interest, such as about 70%, 75%, 80%, 85%, 90%, 95%, 96%, 97%, 98%, 99%, 99.5%, or 99.9% identity. A variant may be substantially identical to the sequence of interest. A variant may be a single-stranded (ss) or double-stranded (ds) DNA molecule. A dsDNA variant may be the product of an amplification reaction. A ssDNA variant may be a strand of a dsDNA variant that has dissociated from its complementary strand, e.g., if the complementary strand was degraded. As used herein, the term "megaprimer" is interchangeable with the term "ssDNA variant."

"Degrade" means to alter a DNA molecule by cleaving, removing, or replacing nucleobases by treatment with an enzyme or chemical.

"Protected" means that a DNA molecule is degraded more slowly as compared to a non-protected DNA molecule under the same conditions. A protected DNA molecule may be a DNA molecule that is not degraded at all. A protected DNA molecule may a DNA molecule that includes modified nucleobases, nucleobases other than adenine, guanine, cytosine, and thymine, or inter-nucleotide bonds other than phosphodiester bonds, such that degradation of the DNA molecule is inhibited as compared to the degradation of a non-protected DNA molecule. Alternatively, a protected DNA molecule may be a DNA molecule that is not modified in a manner capable of increasing the degradation of the DNA molecule as compared to the degradation of a DNA molecule that is so modified.

"Selective degradation" means that a provided enzyme degrades some DNA molecules more rapidly than others. For example, the enzyme may selectively degrade a non-protected strand over a protected strand. A non-protected strand may be selectively degraded at a rate, for example, of at least about 20-fold greater than the rate at which the protected strand is degraded. For instance, a non-protected strand may be selectively degraded at a rate about 20-, 30-, 40-, 50-, 60-, 70-, 80-, 90-, 100-, 200-, 300-, 400-, 500-, 600-, 700-, 800-, 900-, 1000-, 2000-, 3000-, 4000-, 5000-, or more fold greater than the protected strand. In some cases, the enzyme may not degrade the protected strand at all.

"Phosphorothioate" means an inter-nucleotide bond that may be found in a polynucleotide molecule, such as DNA. Chemically, a phosphorothioate differs from a phosphodiester bond in that one of the non-bridging oxygens is a sulfur atom instead of an oxygen atom.

A "5' phosphorothioate" means a phosphorothioate present in an oligonucleotide, e.g., at the 5' terminal inter-nucleotide bond position. A 5' phosphorothioate may be the terminal 5' bond of an oligonucleotide, or may be separated from the 5' terminal bond by one or more nucleotides. In an oligonucleotide with two or more 5' phosphorothioates, the phosphorothioates may occupy consecutive inter-nucleotide bond positions inclusive of the 5' terminal inter-nucleotide bond position. Alternatively, the phosphorothioates may occupy non-consecutive inter-nucleotide bond positions and the occupied positions may not be inclusive of the 5' terminal inter-nucleotide bond position. The phosphorothioates of an oligonucleotide with two or more 5' phosphorothioates may be consecutive, non-consecutive, or a mixture of consecutive and nonconsecutive phosphorothioates. An oligonucleotide with two or more 5' phosphorothioates may include 2 or more consecutive phosphorothioates, such as 2, 3, 4, 5, 6, 7, 8, 9, 10, 15, 20, 30, 40, 50, or 100 or more consecutive phosphorothioates, or may have no consecutive phosphorothioates. An oligonucleotide with three or more 5' phosphorothioates may include 3, 4, 5, 6, 7, 8, 9, 10, 15, 20, 30, 40, 50, or 100 or more phosphorothioates.

An oligonucleotide with zero, one, or two phosphorothioates is a "non-phosphorothioate oligonucleotide." An oligonucleotide with three or more phosphorothioates is a "phosphorothioate oligonucleotide."

A pair of oligonucleotides will be said to "flank" a sequence of interest in a template DNA molecule if sequences to which the oligonucleotides could hybridize are found on opposite strands of the template DNA molecule such that, were the oligonucleotides aligned to these hybridization sequences, the 3' termini of the oligonucleotides would face toward each other and the sequence of interest would fall between the 5' termini of the oligonucleotides.

An "amplification reaction" means any reaction that generates a copy of a sequence of interest. The copy may be a perfect copy of the sequence of interest or a variant of the sequence of interest. The fidelity of an amplification reaction is dependent upon factors such as the polymerase, nucleotides, buffers and cycling conditions utilized, as well as other factors. Amplification reactions known in the art include polymerase chain reaction (PCR) and error-prone PCR. An amplification reaction may be carried out using two oligonucleotides, such as a protected oligonucleotide and a non-protected oligonucleotide, for example, a phosphorothioate oligonucleotide and a non-phosphorothioate oligonucleotide.

A "protected strand," as used herein, means a DNA molecule produced in an amplification reaction by extension primed from a protected oligonucleotide.

A "non-protected strand," as used herein, means a DNA molecule produced in an amplification reaction by extension primed from a non-protected oligonucleotide.

A "phosphorothioate strand." as used herein, means a DNA molecule that has 3 or more 5' phosphorothioates.

A "non-phosphorothioate strand," as used herein, means a DNA molecule that has less than three 5' phosphorothioates.

An "ssDNA intermediary" means a ssDNA molecule to which a ssDNA variant may hybridize. A ssDNA intermediary may be a vector for transformation. For example, the ssDNA intermediary may be a phagemid.

"Heteroduplex DNA" means a population of molecules made up of ssDNA variants hybridized to ssDNA intermediaries, or a composition derived from such a population of molecules through subsequent processing steps, such as extension, denaturing, or strand-specific digestion, prior to transformation into cells. A "heteroduplex DNA molecule" means a ssDNA variant hybridized to a ssDNA intermediary, or a product derived from such a molecule through subsequent processing steps, such as extension, denaturing, or strand-specific digestion, prior to transformation into cells.

"Purifying" means to separate about 20% to 100% of a desired product, such as about 20%, 30%, 40%, 50%, 60%, 70%, 80%, 90%, or 100% of a desired product, from a starting material.

DETAILED DESCRIPTION

Figure 1:
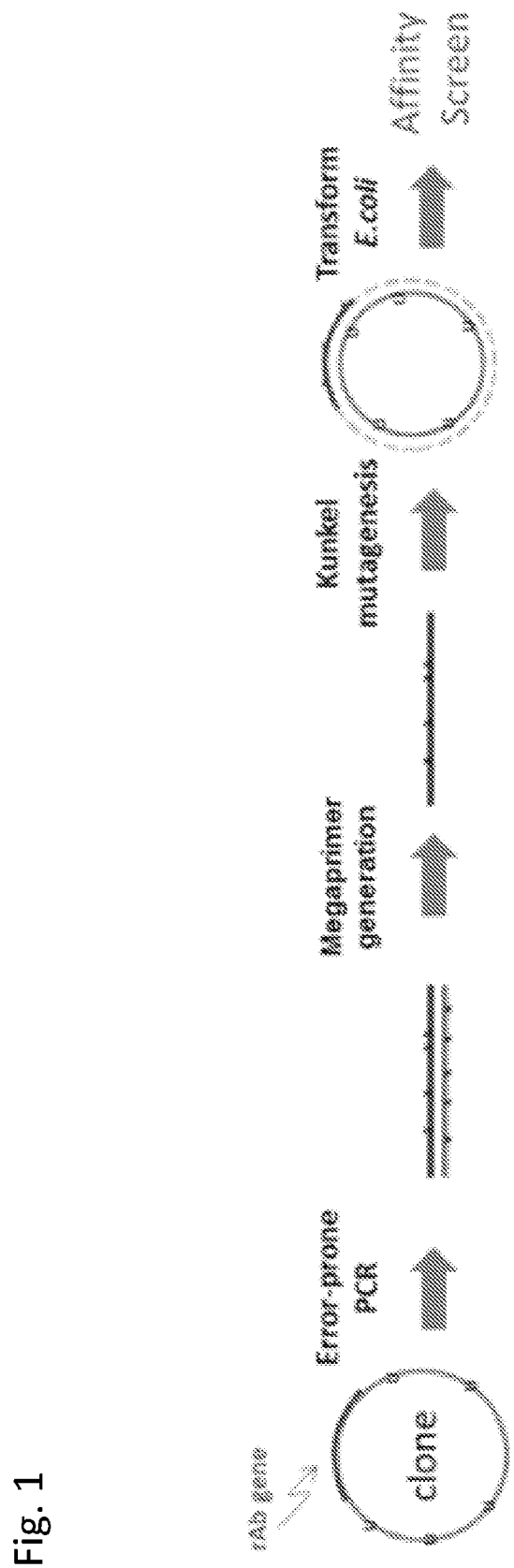
FIG. 1 is a diagram of an example of a method of the present invention. A recombinant antibody sequence of interest is amplified under error-prone PCR conditions. The resulting dsDNA variants are treated with T7 exonuclease to selectively degrade one strand of the dsDNA molecules, resulting in ssDNA variants, or megaprimers. These ssDNA variants (megaprimers) are annealed to uracilated, circular single-stranded phagemids and used to prime in vitro synthesis by DNA polymerase. The ligated heteroduplex products are transformed into an E. coli strain that is capable of removing uracils from DNA and repairing the DNA in favor of the newly synthesized, recombinant strand containing the ssDNA variant.

The process of isolating functional sequences from a library of diverse genetic sequences may be referred to as directed evolution. An efficient method of producing large, diverse libraries of genetic sequences is a critical step in this process. Such a library may be a population of variants of a sequence of interest. The present invention is directed toward an efficient method of generating a library of variants of a sequence of interest, such as may be used in directed evolution. As described in detail below, the method may include an amplification reaction, e.g., error-prone PCR, to generate double-stranded DNA (dsDNA) variants of a sequence of interest, after which one strand of the dsDNA variants may be selectively degraded to produce single-stranded DNA (ssDNA) variants. The ssDNA variants may be hybridized to ssDNA intermediaries, e.g., uracilated circular ssDNA intermediaries, to form heteroduplex DNA. In some embodiments, the heteroduplex DNA is incubated with DNA polymerase to extend the ssDNA variant, using the ssDNA intermediary as a template. Heteroduplex DNA may be transformed into cells, such as *E. coli* cells, yielding a library of variants. This method eliminates the inefficient sub-cloning steps and the need for costly primer sets required by many prior methods.

Sequence of Interest

The present method is also directed toward a library of variants of a sequence of interest. The sequence of interest may be a randomized sequence, a sequence without a known function, or a sequence that encodes a protein. The sequence of interest may encode an enzyme or a domain or fragment thereof, a kinase or a domain or fragment thereof, a transcription factor or a domain or fragment thereof, a DNA binding protein or a domain or fragment thereof, an RNA binding protein or a domain or fragment thereof, an antibody or a domain or fragment thereof, a polymerase or a domain or fragment thereof, or a human protein or a domain or fragment thereof.

Amplification Reaction

In the present method, dsDNA variants may be amplified from a template DNA molecule. The template DNA molecule is a molecule that includes the sequence of interest. The template DNA molecule may be a ssDNA molecule, a dsDNA molecule, a circular ssDNA molecule, a circular dsDNA molecule, a uracilated circular ssDNA molecule, or a uracilated circular dsDNA molecule. The template DNA molecule may be a PCR product, plasmid, phagemid, phage-packaged DNA molecule, or an isolated DNA molecule.

In the present method, a sequence of interest may be amplified using a pair of oligonucleotides, of which one oligonucleotide is a protected oligonucleotide and the other is a non-protected oligonucleotide. The sequence of interest may be amplified using such an oligonucleotide pair by an amplification reaction such as PCR, error-prone PCR, isothermal amplification, or rolling circle amplification.

Various methods of amplification may induce sequence changes by which the sequence of an amplicon differs from the sequence of the template sequence of interest. Certain methods of PCR promote nucleotide misincorporation. Error-prone PCR is an example of such a method. Error-prone PCR may be carried out by any of the methods known in the art. Error-prone PCR is typically a modified form of standard PCR that enhances the rate at which mutations are introduced into sequences amplified from a template sequence. Methods to increase the mutation rate of PCR include increasing the concentration of $MgCl_2$, increasing the concentration of MnCl2, otherwise altering the availability of divalent cations, including unequal proportions of each nucleotide in the PCR reaction, or including nucleotide analogues. Specific methods of error-prone PCR are known in the art. For example, Rasila et al. (*Analytical Biochemistry*, 2009, 388:71-80) describes error-prone PCR with Taq DNA polymerase and mutagenic buffer, and U.S. Pat. No. 6,803,216 describes PCR mutagenesis using a novel error-prone DNA polymerase. Other methods are also known in the art.

Because the use of DNA polymerases in PCR always results in a certain degree of mutation, standard methods of PCR may also be used to produce dsDNA variants of a sequence of interest. Intrinsic error rates of DNA polymerases, both natural and engineered, vary. The amplification reaction products of the present invention may be dsDNA variants of the sequence of interest.

Oligonucleotides

The amplification reaction of the present invention may utilize a pair of oligonucleotides in which one oligonucleotide is a protected oligonucleotide and the other is a non-protected oligonucleotide. Because of the oligonucleotides used in the present invention, each dsDNA variant may have a protected strand and a non-protected strand. The protected strand may be selectively degraded over the non-protected strand, enabling the conversion of dsDNA variants to ssDNA variants.

In one example of the present invention, a phosphorothioate oligonucleotide and a non-phosphorothioate oligonucleotide that flank a sequence of interest are used to amplify the sequence of interest from a template DNA molecule. These oligonucleotides are designed to selectively incorporate three or more 5' phosphorothioates into one strand of the dsDNA variant but not the other. More specifically, one of the oligonucleotides complementary to the sequence of interest (the phosphorothioate oligonucleotide) has three or more 5' phosphorothioates, while a second oligonucleotide complementary to the opposite strand of the sequence of interest (the non-phosphorothioate oligonucleotide) has less than three phosphorothioates.

The phosphorothioate oligonucleotide may include three or more phosphorothioates, e.g., about 3, 4, 5, 6, 7, 8, 9, 10, 15, 20, 30, 40, 50, or 100 phosphorothioates. Preferably, the phosphorothioate oligonucleotide includes between 3 and 100 phosphorothioates, more preferably between 3 and 20 phosphorothioates, or still more preferably between 3 and 10 phosphorothioates. The phosphorothioates may be consecutive or may be distributed throughout the phosphorothioate oligonucleotide. The non-phosphorothioate oligonucleotide may include less than three phosphorothioates, e.g., two, one or zero phosphorothioates. The length of either the phosphorothioate oligonucleotide or the non-phosphorothioate oligonucleotide may be between 8 and 200 basepairs, e.g., about 8, 9, 10, 11, 12, 13, 14, 15, 16, 17, 18, 19, 20, 21, 22, 23, 24, 25, 26, 27, 28, 29, 30, 35, 40, 45, 50, 100, 150, or 200 basepairs.

Because of the oligonucleotides used, each dsDNA variant of the sequence of interest may include a strand with three or more 5' phosphorothioates and a strand with less than three 5' phosphorothioates. The strand with three or more 5' phosphorothioates may be protected from degradation over the strand with less than three 5' phosphorothioates.

In another example of the present invention, the protected oligonucleotide includes a 5' phosphate and the non-protected oligonucleotide does not include a 5' phosphate. The non-protected strand lacking a 5' phosphate may be degraded more quickly than the protected strand, providing a means for the production of ssDNA variants. In some embodiments, a mechanism of providing a protected oligonucleotide may be used in combination with a different mechanism of providing a non-protected oligonucleotide.

Conversion of dsDNA Variants to ssDNA Variants

The present invention utilizes an enzyme, compound, or chemical that selectively degrades the non-protected strand of dsDNA variants to efficiently convert dsDNA variants into ssDNA variants. Typically, DNA hydrolysis is not strand-specific. In the present invention, the selective degradation of a single strand of a dsDNA variant is possible because one stranded is a protected strand while the other is a non-protected strand.

For example, three or more 5' phosphorothioates may protect a strand of DNA from degradation. In contrast, a strand with zero, one, or two phosphorothioates will not be protected. A dsDNA variant in which the protected strand includes three or more 5' phosphorothioates and the non-protected strand includes less than three 5' phosphorothioates may be converted to a ssDNA variant by an enzyme that selectively degrades DNA strands with less than three 5' phosphorothioates.

Examples of exonucleases capable of selectively degrading strands with less than three 5' phosphorothioates include T7 exonuclease and lambda exonuclease. Both T7 and lambda exonucleases hydrolyze double-stranded DNA in the 5' to 3' direction. If one strand of a dsDNA molecule is protected by 5' phosphorothioates and the opposite strand is not, the opposite strand will be selectively degraded by T7 or lambda exonuclease. The unprotected strand may be completely degraded. Selective degradation produces a ssDNA variant. The ssDNA variant can then hybridize to a ssDNA intermediary (e.g., FIG. 1). In another example, the protected oligonucleotide is a nucleotide that includes a 5' phosphate, whereas the non-protected oligonucleotide does not include a 5' phosphate. The non-protected strand may be degraded by an exonuclease more quickly than the protected strand. Lambda exonuclease is an example of a nuclease that may selectively degrade strands without a 5' phosphate over a stand with a 5' phosphate. Treatment of dsDNA variants in which a protected strand includes a 5' phosphate and the non-protected strand does not may convert the dsDNA variants into ssDNA variants.

Incorporation of ssDNA Variants into Heteroduplex DNA

Generating a library of variants of a sequence of interest requires transforming cells with the variants of the sequence of interest. For this to occur, the ssDNA variants can be adapted into a form with which cells, e.g., *E. coli*, may be successfully transfected. In the present invention, the ssDNA variants are incorporated into heteroduplex DNA by hybridization to ssDNA intermediaries. In some embodiments, the ssDNA variants are purified prior to hybridization. The ssDNA variants are incubated with ssDNA intermediaries that include a sequence to which the ssDNA variant may hybridize. In some cases, this sequence will be identical or substantially identical to the sequence of interest. For example, the ssDNA intermediaries may include a sequence that is 30%, 35%, 40%, 45%, 50%, 55%, 60%, 65%, 70%, 75%, 80%, 85%, 90%, 95%, or 100% identical to the sequence of interest.

The ssDNA intermediaries may be circular ssDNA molecules or linear ssDNA molecules. The ssDNA intermediaries may be phagemids or include sequence fragments identical or substantially identical to a phagemid. The ssDNA intermediaries may be modified for the purpose of phage display by various techniques known in the art, e.g., such that the ssDNA variant of the sequence of interest is incorporated into a gene expression mechanism optimized for phage display. The ssDNA intermediaries may be uracilated or methylated.

To hybridize the ssDNA variants to the ssDNA intermediaries, the ssDNA variants and ssDNA intermediaries may be co-incubated at a temperature or series of temperatures that permits hybridization. For example, they may be co-incubated at a denaturing temperature with gradual cooling to an annealing temperature. Methods of hybridization are known in the art. Exemplary temperatures may include denaturing at about 90° C., annealing at about 55° C., and cooling from the denaturing temperature to the annealing temperature at about −1° C. per minute.

The hybridized ssDNA variants may, in certain embodiments, prime DNA extension in the presence of a DNA polymerase and free nucleotides. Extension may be accomplished by incubation of the extension reaction at a temperature at which the DNA polymerase is active. The extension reaction may optionally include a ligase. In some embodiments, in which the ssDNA intermediate is, e.g., uracilated or methylated, complete extension can result in a heteroduplex DNA molecule that includes the original uracilated or methylated strand of the ssDNA intermediary and a new, non-uracilated and/or non-methylated strand having the same sequence as the ssDNA intermediary, excepting changes or differences present in the ssDNA variant that have been incorporated and any additional changes or differences introduced during extension.

In some embodiments, heteroduplex DNA may be treated in vitro, prior to transformation, in order to selectively degrade the ssDNA intermediary strands. This may be accomplished by denaturing the heteroduplex DNA and treating the denatured heteroduplex DNA with an enzyme, compound, or chemical capable of selectively degrading the ssDNA intermediary strands. For instance, if the ssDNA intermediary strands, but not the ssDNA variant strands, include modified nucleobases or nucleobases other than adenine, guanine, cytosine, and thymine, particular enzymes may selectively degrade the ssDNA intermediaries in vitro. In one example, the ssDNA intermediary strands include methylated adenine nucleobases and the denatured heteroduplex DNA is treated with the enzyme DpnI, which selectively degrades methylated DNA. Alternatively, the ssDNA variant strands may include modified nucleobases or nucleobases other than adenine, guanine, cytosine, and thymine, that are not found in the ssDNA intermediary strands and that selectively protect the ssDNA variant strands from degradation. In one example, the ssDNA variant strands, but not the ssDNA intermediary strands, include methylated nucleobases and the denatured heteroduplex DNA is treated with the enzyme Sau3Al, which selectively degrades non-methylated DNA. A modification or atypical base present in strands of one group may be fully or only partially absent from strands of the other.

Incorporation of ssDNA Variants from Two or More ssDNA Variant Populations into Heteroduplex DNA In some embodiments, ssDNA variants derived from a single sequence of interest may be hybridized to an ssDNA intermediary. In other embodiments, ssDNA variants derived from two or more different sequences of interest may hybridize to an ssDNA intermediary. For example, ssDNA variants may be generated from dsDNA generated from each of two or more different sequences of interest. Any two different sequences of interest may be found in a single template DNA sequence or in different template DNA sequences. As such, any two or more different populations of dsDNA variants may be amplified from a single template DNA molecule or from two or more different template DNA molecules.

A single pair of oligonucleotides, including a protected oligonucleotide and a non-protected oligonucleotide, may be capable of amplifying two or more sequences of interest. Alternatively, two or more different pairs of oligonucleotides, each pair capable of amplifying one or more sequences of interest, may be used to amplify two or more sequences of interest. The mechanism by which the protected oligonucleotide of a given pair of oligonucleotides is selectively protected from degradation over the non-protected oligonucleotide may be the same for any two pairs of oligonucleotides or different for any two pairs of oligonucleotides.

The production of a population of dsDNA variants from each of any two sequences of interest may be carried out separately, such that ssDNA variants generated from each sequence of interest are physically separated. For instance, amplification of any two different sequence of interest may be carried out in separate reaction chambers. Any two amplification reactions carried out separately may be the same type of amplification reaction, e.g., both error-prone PCR, or different types of reactions, e.g., one reaction may be error-prone PCR while the other may be standard PCR or isothermal amplification. Alternatively, amplification of any two sequences of interest may be carried out in a single reaction. Similarly, conversion of any two populations of dsDNA variants to ssDNA variants may be carried out separately or in a single reaction. Conversion of dsDNA variants may be accomplished by any mechanism of selective degradation, the applicability of which may be determined by the oligononucleotides utilized in each amplification reaction.

Two or more separately generated populations of ssDNA variants may be combined prior to or during hybridization to ssDNA intermediaries. The ssDNA intermediaries may include a sequence substantially identical to each of the sequences of interest. A single sequence may be substantially identical to more than one sequence of interest. Alternatively, a single sequence may be substantially identical only one sequence of interest. Any two sequences of interest may be substantially identical to a single sequence of the ssDNA intermediaries, to overlapping sequences of the ssDNA intermediaries, or to non-overlapping sequences of the ssDNA intermediaries. A ssDNA intermediary may comprise multiple overlapping or non-overlapping sequences to which a single sequence of interest may hybridize. Hybridization of populations of ssDNA variants to ssDNA intermediaries may occur simultaneously or sequentially. Combined populations of ssDNA variants may be hybridized to ssDNA intermediaries by the methods described above, and the resulting heteroduplex DNA may be appropriate for utilization in any post-hybridization step, treatment, or reaction of the present invention. Any of the steps, reactions, or treatments described may occur in parallel, meaning that they occur in a manner that permits the incorporation of different ssDNA populations into a single heteroduplex DNA. Steps, reactions, or treatments occurring in parallel may or may not occur simultaneously or within a similar period of time. A method of hybridizing two or more populations of ssDNA variants to a ssDNA intermediary may comprise the generation of ssDNA intermediaries from two or more sequences of interest, such as 2, 3, 4, 5, 6, 7, 8, 9, 10, 12, 14, 16, 18, or 20 sequences of interest.

An example of a use of a method of hybridizing two or more populations of ssDNA variants to a ssDNA intermediary may be to modify multiple sequence fragments within a sequence encoding a protein of interest. For example, an antibody may have a fixed framework and multiple non-contiguous complementarity determining regions (CDRs) that determine antibody function. The sequence encoding each CDR, or a fragment thereof, may be a sequence of interest. By generating ssDNA variants from each CDR sequence of interest in a method of the present invention, a library of variants of a sequence of interest with sequence changes only in regions where variation was desired (CDRs) and not others (the fixed framework) may be generated. These variants of the sequence of interest may be used in a method of directed evolution to identify antibodies with particular functions.

Transformation of Cells with Heteroduplex DNA or ssDNA Variant Strands Produced by Selective In Vitro Degradation of Heterduplex DNA Intermediary Strands Transformation of cells with heteroduplex DNA or ssDNA variant strands produced by selective in vitro degradation of heterduplex DNA intermediary strands may accomplished by any method known in the art. Examples include electroporation, chemical transformation, and heat shock transformation. Cells may be treated to optimize competence for the selected method of transformation. In some embodiments, heteroduplex DNA may be purified prior to transformation. Transformation may include the transformation of 1 to 50 or more aliquots. For example, 1, 5, 10, 15, 20, 25, 30, 35, 40, 45, or 50 aliquots may be transformed. The transformants are a library of variants of the sequence of interest. Transformants may be cultured in a recovery media. Individual aliquots may be combined in recovery media or cultured separately. After recovery, the cultured transformants may be pelleted. Pelleted transformants may be stored at a temperature of −20° C. or less. Alternatively, pelleted transformants may be resuspended. The resuspended library may be incubated with a helper phage, resulting in a phage display library. Alternatively some or all aliquots of the resuspended library may be stored at a temperature of −20° C. or less. The phage display library may be pelleted. The pelleted phage display library may be stored at a temperature of −20° C. or less. Alternatively, the pelleted phage display library may be resuspended. The resuspended pelleted phage display library may be stored at a temperature of −20° C. or less. A cultured library of variants, resuspended library of variants, phage display library, or resuspended phage display library may be optionally diluted and plated onto culture plates.

The cells of the present invention may be the cells of a eukaryote, such as a mammal, an insect, or yeast, or the cells of bacteria, such as *E. coli* or *B. subtilis*. Embodiments utilizing uracilated ssDNA intermediaries may transform cells capable of selectively degrading uracilated DNA, such as Ung+ *E. coli*. Embodiments utilizing methylated ssDNA intermediaries may transform cells capable of selectively degrading methylated DNA, such as Mcr+ bacteria.

Resolution of Mismatch Nucleotides

Heteroduplex DNA, or ssDNA variant strands produced by selective in vitro degradation of heterduplex DNA intermediary strands, may be resolved, meaning that the heteroduplex DNA or ssDNA variant strands may be modified by in vitro or in vivo processes to generate a double stranded vector with few or no mismatch nucleotides. A resolved vector can incorporate the sequences of one or more ssDNA variants having one or more, if any, changes or differences present in comparison to the sequence of interest. In some instances, a resolved vector is formed by an in vitro or in vivo reaction in which one or more mismatched nucleotides of an intermediary strand of heteroduplex DNA to which one or more ssDNA variants are hybridized are modified such that the mismatch nucleotide of the intermediary strand is replaced (i.e., repaired) with a nucleotide complementary to a hybridized ssDNA variant strand. Repair may also occur such that one or more mismatched nucleotides of an ssDNA variant strand are modified such that the mismatch nucleotide of the ssDNA variant strand is replaced with a nucleotide complementary to a segment of the intermediary strand to which it is hybridized.

An intermediary strand of heteroduplex DNA may include modifications that facilitate repair in a manner that conserves (i.e., favors) the sequence of the ssDNA variant strand. In some embodiments, an ssDNA variant strand may include modifications that facilitate repair in a manner that favors the sequence of the ssDNA variant strand. In particular instances, the intermediary strand is uracilated. In still more particular instances, the DNA is transformed into an ung+ bacterial cell, such as an ung+ *E. coli* cell.

In other instances, an ssDNA variant strand produced by selective in vitro degradation of the heterduplex DNA intermediary strand is resolved in vivo. Such resolution may occur, e.g., by the generation of a new DNA strand complementary to the ssDNA variant strand.

In Vivo Degradation of Non-Recombinant Vectors

The present invention includes, for use in conjunction with or independently of one or more or all embodiments of the present invention, a method of degrading non-recombinant vectors. In embodiments including the degradation of non-recombinant vectors, a recipient vector includes one or more restriction sites within one or more segments to be removed, replaced, or otherwise modified. After the one or more segments are removed, replaced, or otherwise modified, e.g., by cloning, a cell-expressed restriction enzyme can selectively degrade the intermediary strand. For instance, in some embodiments, the restriction site or sites are SacII sites and the restriction enzyme is Eco29kI (described, e.g., in Pertzev et al. Nucleic Acids Res. 1992 Apr. 25; 20(8): 1991, which is herein incorporated by reference). Eco29kI is a SacII isoschizomer capable of cleaving the SacII restriction site (CCGCGG) and that may be expressed in bacterial cells, e.g., in *E. coli*. One advantage of the SacII restriction site is that it does not include A or T nucleotides, allowing optimal use of dut and ung strategies in combination with various embodiments of the present invention. The cells may be, e.g., bacterial cells such as *E. coli* cells, or, more particularly, such as TG1 cells. As a result, vectors in which each of the one or more segments are not modified, replaced, or removed, such that a resulting vector does not include a restriction site, will be degraded within the cells expressing the restriction enzyme or enzymes.

In particular embodiments, the in vivo degradation of non-recombinant vectors or vector strands can be used to facilitate the recombination of immunoglobulin such that the scFv variable regions and IgG constant regions are arranged in the form of an immunoglobulin. The scFv can include a light chain variable domain, linker, heavy chain variable domain, and Gp3 protein. In some embodiments, a nucleic acid encoding at least an IgG heavy chain constant domain includes a segment that includes a restriction site and a nucleic acid encoding at least an IgG heavy chain constant domain. The IgG heavy chain can include a segment that includes a restriction site. The heavy chain and light chain nucleic acids may be present on separate vectors, on a single vector, or arranged in a bi-cistronic expression system. In particular embodiments, the scFv light chain variable domain and heavy chain variable domain are respectively cloned into the nucleic acid encoding the IgG light chain constant domain and the nucleic acid encoding the IgG heavy chain constant domain such that the cloning removes or modifies the respective restriction sites and results in the formation of a nucleic acid encoding an IgG heavy chain and a nucleic acid encoding an IgG light chain. As noted above, these two constructs may be present on separate vectors (e.g., for expression within a single cell) or a single vector (e.g., for separate expression or in a bi-cistronic arrangement).

In particular embodiments, the restriction site is a SacII restriction site. In particular embodiments, the in vivo degradation is by Eco29kl. In particular instances, the intermediary strand is uracilated. In still more particular instances, the DNA is transformed into an ung+ bacterial cell, such as an ung+ *E. coli* cell.

Figure 8:
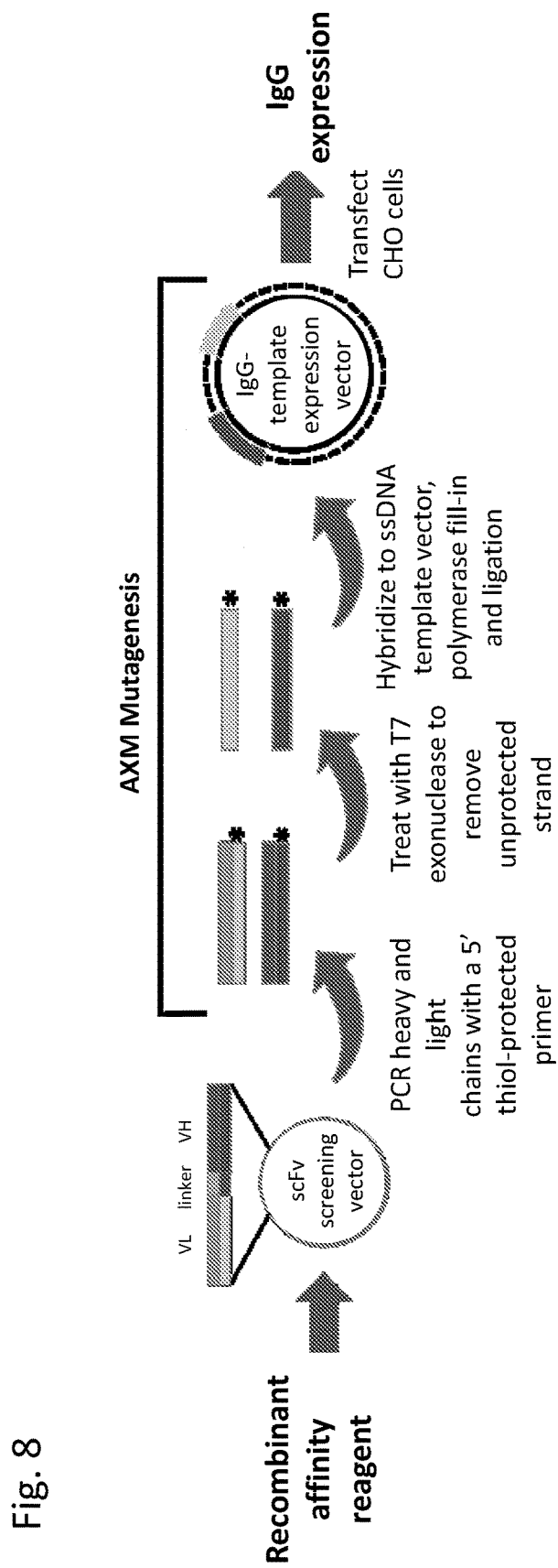
FIG. 8 is a diagram showing mutagenesis of heavy and light immunoglobulin domains

Vectors described, generated, or capable of being generated by the methods described herein may be suited for transfer into a non-bacterial cell type, e.g., CHO cells. Vectors may include sequence information sufficient to direct expression of one or more proteins present in the vectors in one or more cell types, e.g. mammalian cells, insect cells, and/or bacterial cells. As a non-limiting example, a vector generated by a method of the present invention may include an IgG heavy chain and an IgG light chain capable of expression in CHO cells (FIG. 8).

Degradation of Vectors that Resolve in Favor of the ssDNA Intermediary Strand or do not Sufficiently Incorporate ssDNA Variants In any of the various embodiments of the present invention, a mechanism for the selective degradation of vectors that resolve in favor of an ssDNA intermediary strand or that do not sufficiently incorporate ssDNA variants can be provided. In particular, an ssDNA intermediary may include one or more segments including one or more restriction sites (e.g., sequences that can be recognized and cleaved by a restriction enzyme), while ssDNA variants capable of hybridizing to the ssDNA intermediary strand segments do not include those restriction sites. Accordingly, in general, if the restriction sites are repaired in favor of the ssDNA variants, the resolved vector will not be degraded by restriction enzymes capable of cleaving those sites. In contrast, if one or more of the restriction sites repair in favor of the ssDNA intermediary, the resulting vector will be susceptible to cleavage by restriction enzymes capable of cleaving those sites.

In one example, an ssDNA intermediary includes a single copy of a particular restriction site and the restriction site is located within a region to which an ssDNA variant is capable of hybridizing. The ssDNA variant does not include the restriction site in any orientation. Accordingly, the restriction site includes one or more mismatched nucleotides, which may be repaired, e.g., in vivo. If the restriction site mismatch is repaired in favor of the ssDNA variant, the resulting vector will not be susceptible to degradation by the particular restriction enzyme. Alternatively, if the restriction site mismatch is repaired in favor of the ssDNA intermediate, the resulting vector will include a restriction site and will be susceptible to degradation by the particular enzyme. In specific examples, the ssDNA intermediary is uracilated.

In various embodiments, the ssDNA variant does not include the restriction site because the restriction site was not present in the template molecule based upon which the ssDNA variant was generated. In other embodiments, the ssDNA variant does not include the restriction site because the restriction site was disrupted by a mutagenic event. Various embodiments of the present invention, as described above, can include ssDNA variants derived from two or more different sequences of interest and that are capable of hybridizing to an ssDNA intermediary. In such instances, segments of the ssDNA intermediary to which each of the two or more ssDNA variants are capable of hybridizing may each include a restriction site. In some instances, each of the two or more segments to which the ssDNA variants are capable of hybridizing include the same particular restriction site. In other embodiments, the two or more segments to which the ssDNA variants are capable of hybridizing include two or more distinct restriction sites.

In certain instances, one or more segments of an ssDNA intermediary to which one or more ssDNA variants are capable of hybridizing can each include a single restriction site. In other embodiments, the segments of the ssDNA intermediary to which one or more ssDNA variants are capable of hybridizing can include two or more restriction sites.

In some embodiments, one or more resolved vectors are isolated and/or purified and treated with one or more restriction enzymes in vitro to degrade vectors that resolve in favor of an ssDNA intermediary strand or that do not sufficiently incorporate ssDNA variants.

In some embodiments, one or more vectors that resolve in favor of an ssDNA intermediary strand or that do not sufficiently incorporate ssDNA variants are degraded in vivo. In particular, the resolved vector may be present in a cell that expresses a restriction enzyme and include one or more restriction sites that the restriction enzyme is capable of degrading. In still more particular embodiments, the resolved vector may be present in a cell that expresses the restriction enzyme Eco29kl. The cell can be, e.g., a bacterial cell such as an *E. coli* cell, such as a TG1 cell.

Figure 5:
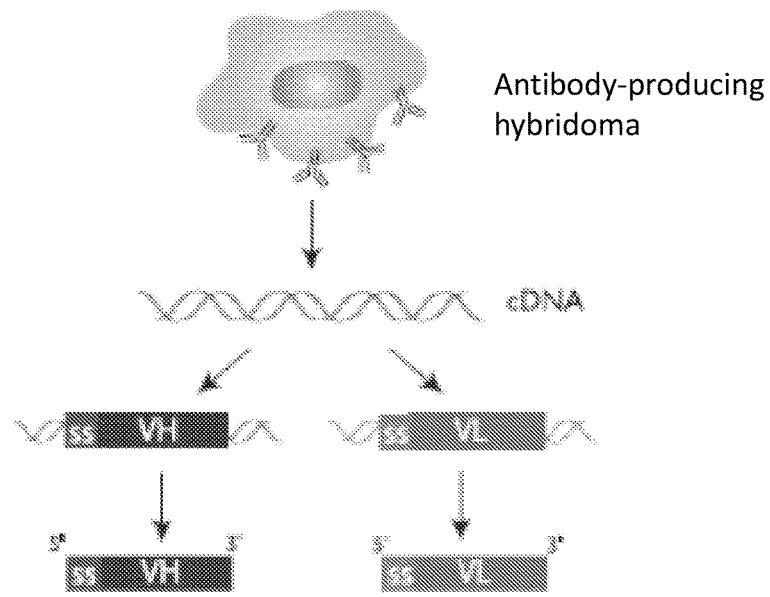
FIG. 5 is a diagram showing the cloning of heavy and light chain variable sequences into separate vectors to be transferred into the same cell for expression of an immunoglobulin.
Figure 5:
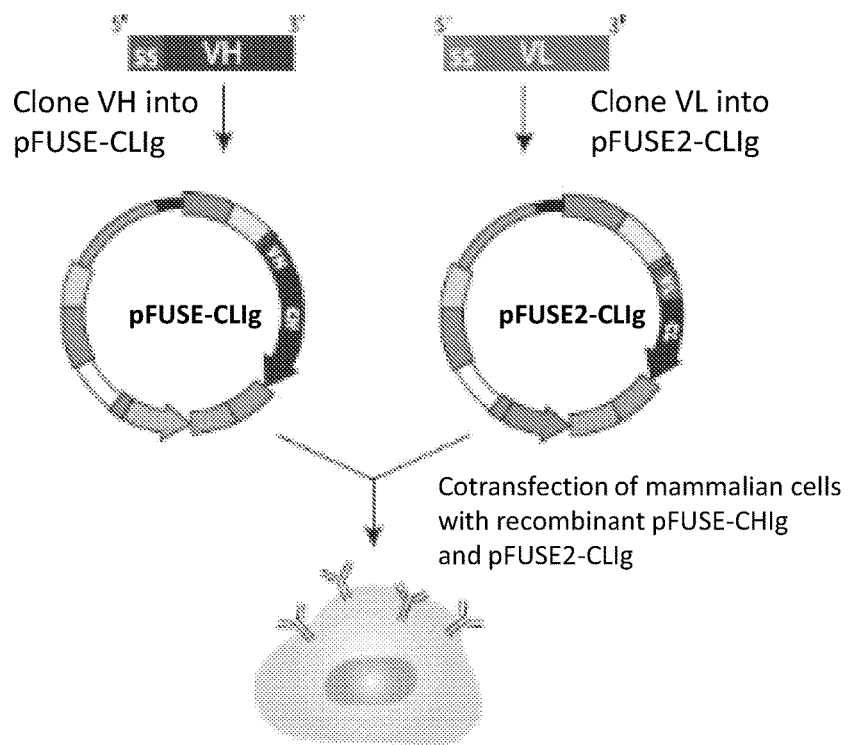
Figure 6:
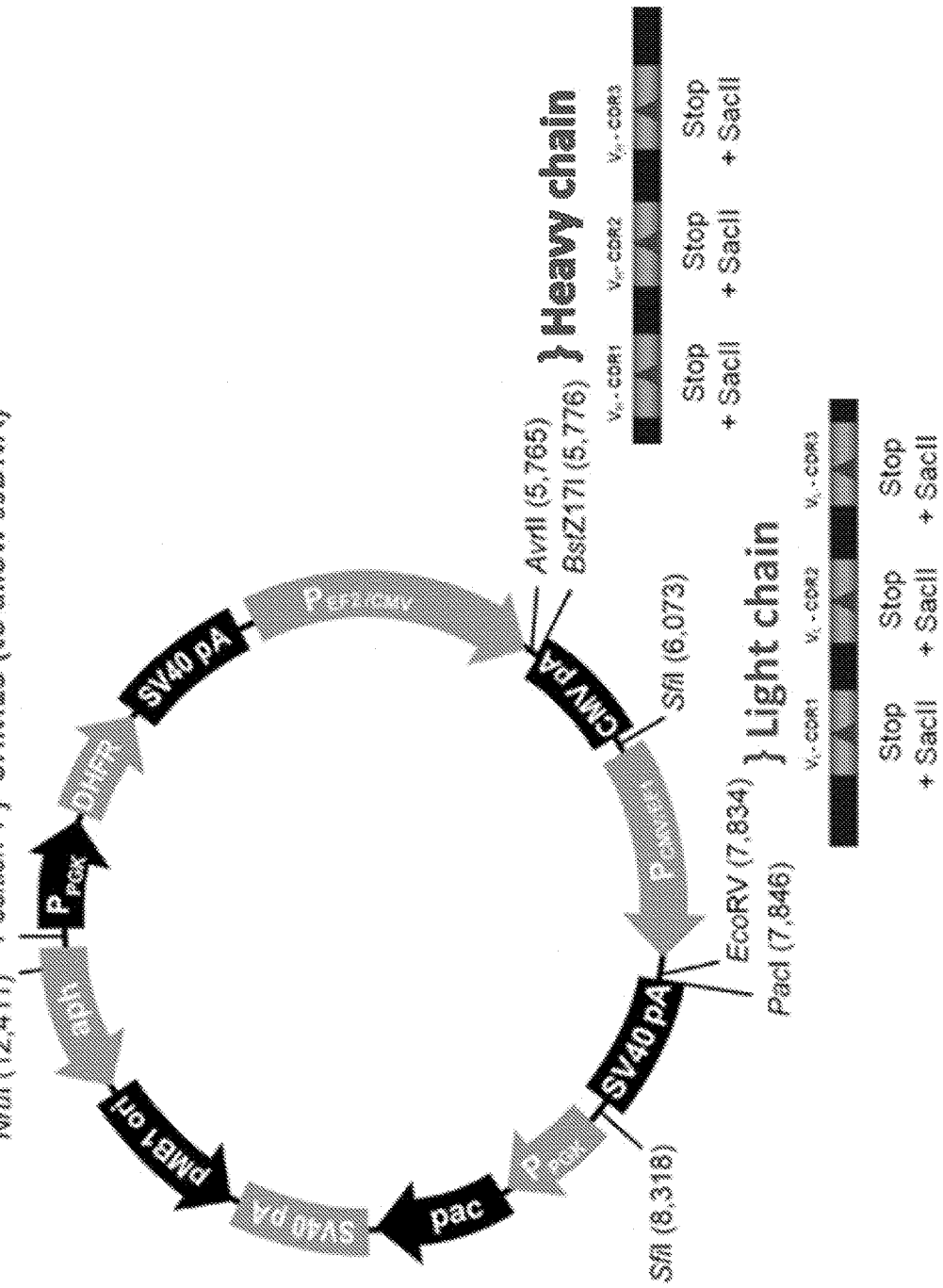
FIG. 6 is a diagram showing a vector into which a heavy chain sequence and a light chain sequence can be inserted, e.g., for bi-cistronic expression.
Figure 7:
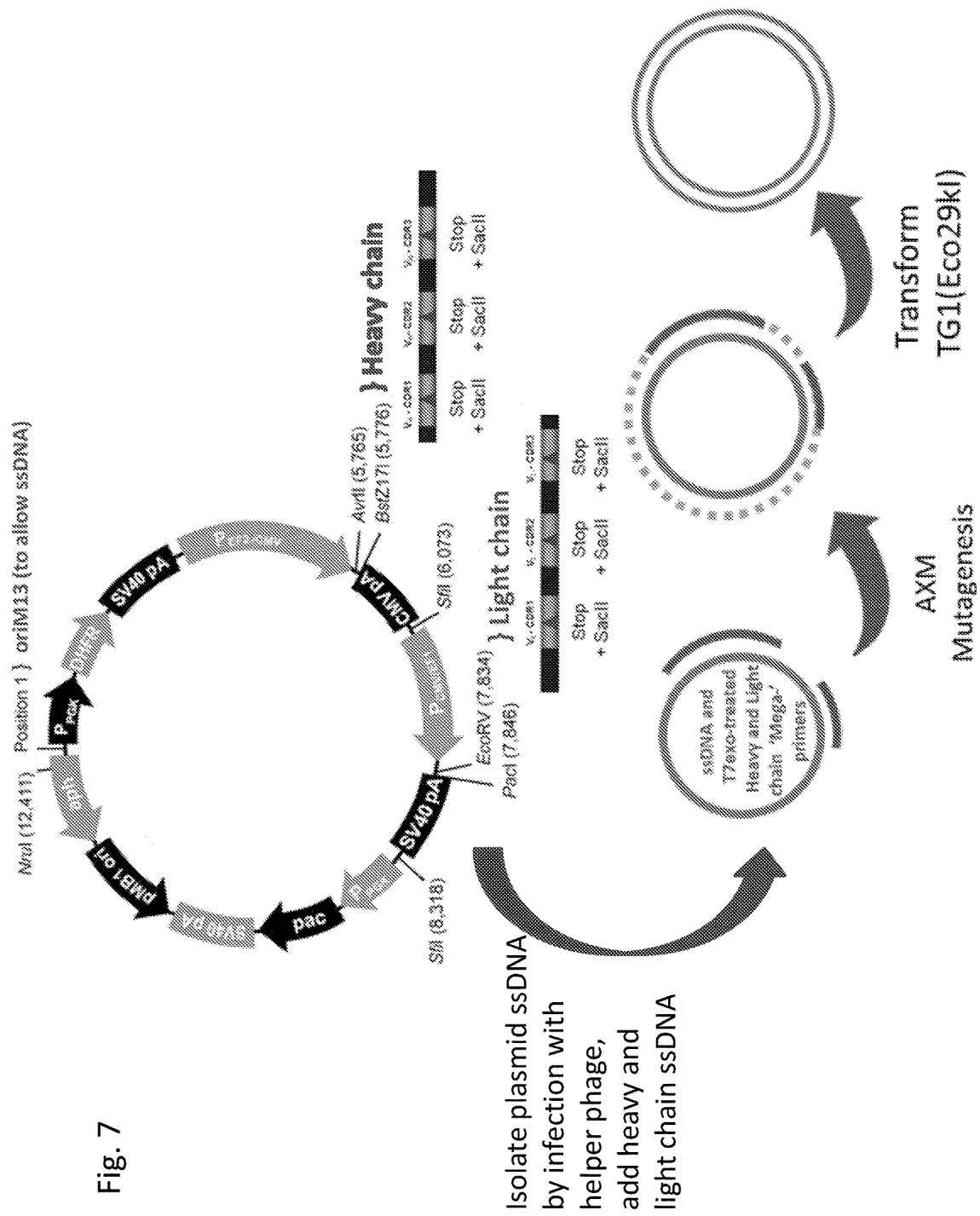
FIG. 7 is a diagram showing mutagenesis of heavy and light immunoglobulin chain sequences with subsequent transformation into TG1 cells having Eco29kI.

In particular embodiments, the in vivo degradation of non-recombinant vectors can be used to facilitate the recombination of ssDNA variants of heavy and light chain variable regions and IgG constant regions in the form of an immunoglobulin. The light chain variable domain and heavy chain variable domain can be, e.g., an scFv light chain variable domain and heavy chain variable domain. In some embodiments, a nucleic acid encoding at least an IgG heavy chain constant domain includes a segment that includes a restriction site and a nucleic acid encoding at leads an IgG light chain constant domain includes a segment that includes a restriction site. The heavy chain and light chain nucleic acids may be present on separate vectors, on a single vector, or arranged in a bi-cistronic expression system (see, e.g., FIGS. 5-7). In particular embodiments, the light chain variable domain and heavy chain variable domain are respectively hybridized to the nucleic acids encoding the IgG light chain constant domain and the nucleic acid encoding the IgG heavy chain constant domain such that resolution of the hybridized vectors removes or modifies the respective restriction sites. This results in the formation of a nucleic acid encoding an IgG heavy chain and a nucleic acid encoding an IgG light chain, each potentially incorporating one or more ssDNA variants. As noted above, these two constructs may be present on separate vectors (e.g., for expression within a single cell) or a single vector (e.g., for separate expression or in a bi-cistronic arrangement). Constructs may be transferred into, e.g., bacteria and may resolve therein.

In particular embodiments, the restriction site is a SacII restriction site. In particular embodiments, the in vivo degradation is by Eco29kl and the bacteria are bacteria expressing Eco29kl.

Vectors described, generated, or capable of being generated by the methods described herein may be suited for transfer to a non-bacterial cell type, e.g., CHO cells. Vectors may include sequence information sufficient to direct expression of one or more proteins present in the vectors in one or more cell types. As a non-limiting example, a vector generated by a method of the present invention may include an IgG heavy chain and an IgG light chain capable of expression in CHO cells (FIG. 8). The above methods and compositions for degradation of vectors that resolve in favor of the ssDNA intermediary strand or do not sufficiently incorporate ssDNA variants can improve the recovery of recombinant nucleic acids, sufficiently recombinant nucleic acids, or nucleic acids recombinant at each of a plurality of targeted loci by 10% or more, such as 10%, 20%, 30%, 40%, 50%, 75%, 100%, 150%, 200%, 300%, 500%, or 1000% or more.

Size and Characteristics of a Library of Variants of a Sequence of Interest

The method of the present invention may yield a library of variants with a total number of variants greater than about 1E+05, such as about 1E+05, 1E+06, 1E+07, 1E+08, 1E+09, 1E+10, 1E+11, or 1E+12 variants or more. Of the transformants produced by the method of the present invention, the number of recombinant transformants may be greater than 30%, such as about 30%, 40%, 50%, 60%, 70%, 80%, 90%, or 100%. The mutation rate amongst recombinants may be at least about 0.75%, such as about 0.75%, 0.8%, 0.85%, 0.9%, 0.95%, 1%, 1.5%, 2%, 2.5%, or 3%. The size of a library, the percentage of recombinants, and the mutation rate amongst recombinants will depend upon the number of heteroduplex DNA molecules, the number of transformations attempted, the method of transformation, the method of amplifying the sequence of interest, and other factors.

Determining the Efficiency of Mutagenesis

The methods of the present invention may be used to produce a library of variants of a sequence of interest. In some embodiments of the methods described herein, it is advantageous to determine the efficiency of mutagenesis. Mechanisms for determining the efficiency of mutagenesis may be quantitative, semi-quantitative, or qualitative.

In one mechanism of determining the efficiency of mutagenesis, a blue/white reporter screen is used in conjunction with the methods of the present invention. Some known constructs for use in a blue/white reporter screen include the LacZ gene. In such embodiments, expression of LacZ may be constitutive, inducible, e.g. by IPTG, or regulated by a plurality of means including, e.g., repression. The LacZ gene may be present in the genome of a cell, on a plasmid, in a heteroduplex DNA molecule of the present invention, or in a resolved vector of the present invention. Expression of the LacZ gene produces β-Galactosidase, an enzyme capable of cleaving X-gal in a manner that results in a blue pigment. Cells including sufficient amounts of β-Galactosidase and X-gal will be blue. Mutagensis may disrupt the cleavage of X-gal by β-Galactosidase. When this occurs, cells will appear white. Furthermore, the percentage of white colonies is indicative of the efficiency of mutagenesis. A high percentage of white colonies indicates that mutations sufficient to disrupt expression of LacZ and/or cleavage of X-gal by β-galactosidase occurred often, while a low percentage of white colonies indicates that such mutations did not occur often.

In certain embodiments, the percentage of white colonies may be experimentally or theoretically correlated with a particular frequency of mutagenesis, whereby the percentage of white colonies provides an estimate of the efficiency of mutagenesis.

In certain embodiments, the cells in which the blue/white screen is applied are experimental cells, e.g., cells including a sequence having been mutagenized in order to identify variants having particular characteristics. In other embodiments, the cells are control cells mutagenized in parallel with experimental cells.

In various other embodiments of the present invention, the screen identifies a phenotype other than blue pigmentation. In such instances, the marker construct is not necessarily a construct that includes a lacZ gene, but rather a construct that includes some other marker gene capable of manifesting a detectable phenotype. For instance, the detectable phenotype capable of being disrupted by mutagenesis may be, without limitation, luminescence, fluorescence, antibiotic resistance, antibiotic sensitivity, toxin resistance, toxin sensitivity, altered growth rate, altered response to an analyte, altered cell structure, altered colony formation, or altered auxotrophy. Additional detectable phenotypes are known in the art. Furthermore, genes capable of manifesting these detectable phenotypes are also known in the art. For example, a detectable phenotype may result from expression of green fluorescent protein (e.g., gfp), a red fluorescent protein (e.g., rfp), a yellow fluorescent protein (e.g., yfp), an ampicillin resistance gene (amp), a tetracycline resistance gene (tet), a kanamycin resistance gene (kan), beta galactosidase (β-Gal), an alanine synthesis gene (e.g., argA), a cystein synthesis gene (e.g., cysE), a leucine synthesis gene (e.g., lysA), a threonine synthesis gene (e.g., thrC), or any of a plurality of other natural or synthetic genes known in the art. Alternatively, the marker protein may be a functional cassette that directs or contributes to the expression of a gene that manifests a detectable phenotype, e.g., by expression of a transcription factor. In such instances, the gene that manifests the detectable phenotype may be endogenous to a cell or encoded by a vector. In embodiments in which a subset of cells are expected to fail to develop under the assay conditions, a replica plate to permissive conditions or another technique of similar effect may be used to determine the percentage of cells having the indicated phenotype. Further, methods for selecting or isolating cells having a detectable phenotype are known in the art. Selecting or isolating one or more cells having a phenotype resulting from expression of a marker protein may include, depending upon the detectable phenotype, flow cytometry, culturing a population of cells in the presence of the relevant antibiotic or toxin, culturing a population of cells in the presence or absence of a particular organic compound, or microscopy techniques. Additional methods of selecting and isolating cells having particular detectable phenotypes are known in the art.

Directed Evolution

A library of variants of the present invention may be utilized in a method of phage display or directed evolution. The ssDNA intermediaries of the present invention may be phagemids appropriate for use in phage display, examples of which are known in the art. Incubation of cells of a library of variants of a sequence of interest with a helper phage may result in the display of proteins encoded by the variants of the sequence of interest. Cells displaying protein variants may be co-incubated with one or more target molecules, such as one or more proteins, molecules, or compounds, with which a protein variant may interact. The target molecule(s) may be a small molecule, a protein or domain thereof, a human protein or domain thereof, an enzyme, a pathogen protein or domain thereof, an antibody or domain thereof, or a recombinant protein. The protein variant may bind, cleave, or modify the target molecule(s). Alternatively, or additionally, the protein variant of the sequence interest may induce a conformational change in the target molecule(s) or catalyze a reaction of the target molecule(s). Sequences identified by directed evolution may be used as the sequence of interest in a subsequent round of diversification and selection.

Example 1: Production of Uracilated Circular ssDNA

In the present invention, uracilated circular ssDNA may serve as the DNA template molecule, the uracilated circular ssDNA intermediary, or both. The uracilated circular ssDNA molecule may be a phage or phagemid ssDNA molecule. One method of producing a uracilated circular ssDNA molecule utilizes CJ236 E. coli cells (Genotype: FΔ(HindIII)::cat (Tra$^+$ Pil$^+$ Cam$^R$)/ung-1 re/A1 dut-1 thi-1 spoT1 mcrA; New England Biolabs). Cells of this strain lack functional dUTPase and uracil-N glycosylase. First, an aliquot (25 µl) of electrocompetent CJ236 cells were pipetted into a chilled 0.1 mm gap cuvette, and 1 µl of pAPIII6 plasmid DNA was added to the CJ236 cells. The cells were electroporated at 1.6 volts in a BioRad electroporator. Immediately after electroporation, 1 ml of SOC media was added and the media plus cells were transferred to a 14 ml Falcon-brand culture tube. The culture was incubated at 37° C. with shaking (~225 rpm) for 1 hour. At the end of the hour, 250 µl of the transformed cells were spread directly on a LB +CAM +AMP plate. These plates were incubated overnight at 37° C.

To produce phage, 1 ml of growth media containing LB and ampicillin (60 µg/ml) and 100 µl of M13K07 helper phage (NEB, 10$^{11}$ PFU/ml) were added to a culture tube. The media was then inoculated with 30 colonies from an overnight transformation plate using a single 10 µl pipette tip. The culture was shaken at 200 rpm at 37° C. for two hours, after which 0.5 µl of Kanamycin stock (final concentration 30 µg/ml) was added and the culture was shaken at 225 rpm at 37° C. for 6 hours or until cloudy. The culture was diluted into 30 ml of fresh 2YT media containing ampicillin (60 µg/ml), Kanamycin (30 µg/ml), and uridine (0.3 µg/ml) in a 250 ml glass baffled flask. The culture was shaken at 225 rpm overnight (approximately 18 hours) at 30° C.

After shaking overnight, the 30 ml culture was transferred to a round bottom centrifuge tube and the cells were pelleted by centrifugation for 15 minutes at 15,000 rpm in a Sorvall RC-5B centrifuge using a SS34 rotor, or an equivalent rotor, at 4° C. The supernatant was filtered using a 0.22 µm tube top filter and the filtrate was transferred to a new round bottom tube containing 6 ml 20% PEG8000/2.5 M NaCl. Each tube was covered with parafilm and inverted several times to mix and then incubated 60 minutes on ice. Each tube was centrifuged at 4° C. for 20 minutes at 10K rpm in the Sorvall RC-5B centrifuge using a SS34 rotor. The supernatant was decanted and the tube centrifuged again at 5K rpm in the Sorvall RC-5B centrifuge using a SS34 rotor for 5 minutes. The remaining liquid was aspirated using a pipette, leaving a phage pellet. The phage pellet was resuspended in 500 µl of 1× sterile PBS and transferred to a 1.7 ml tube. The resuspended phage was centrifuged for 5 minutes at 4° C. in a bench top microcentrifuge at 4° C. at top speed (14K rpm).

The supernatant of the centrifuged resuspended phage was transferred to a new 1.5 ml tube. Next, 7 µl of buffer MP (Qiagen M13 Kit) was added to the phage prep and mixed, followed by incubation at room temperature for 5 minutes. The sample was applied to a QIAprep spin column (Qiagen M13 Kit). The column was centrifuged for 30 seconds at 8K rpm in a bench top microcentrifuge and the flow through was discarded. 700 µl of buffer MLB was then added to the column (Qiagen M13 Kit) and the column was centrifuged at 8K rpm in a bench top microcentrifuge for 15 seconds. 700 µl of additional buffer MLB was added to the column and the column was incubated at room temperature for at least 1 minute, then centrifuged at 8K rpm in a bench top microcentrifuge for 30 seconds. Next, 700 µl of buffer PE (Qiagen M13 Kit) was added and the column was centrifuged at 8K rpm for 15 seconds in a bench top microcentrifuge. This step was repeated. The column was transferred to a fresh 1.7 ml tube. 100 µl of buffer EB (M13 kit) was added to the column membrane and the column was incubated at room temperature for 10 minutes and then centrifuged for 30 seconds at 8K rpm in a bench top centrifuge. The eluent, which contained the dU-ssDNA, was analyzed by running 1.0 µl of the eluent on a 1% agarose TAE gel. DNA appeared as a predominant single band, but faint bands of lower electrophoretic mobility were often visible, likely caused by secondary structure in the dU-ssDNA.

Example 2: Error Prone PCR

In the present invention, error-prone PCR can be utilized to generate variants of a sequence of interest. In this example, one PCR primer is modified at its 5' end by the introduction of phosphorothioates. The sequence of interest is amplified using an oligonucleotide that has three or more 5' phosphorothioates and is capable of hybridizing to one strand of the sequence of interest, and a second oligonucleotide with less than three phosphorothioates capable of hybridizing the opposite strand of the sequence of interest. To perform error-prone PCR, 10 µL of 10× mutagenic PCR buffer [70 mM MgCl$_2$, 500 mM KCl, 100 mM Tris (pH 8.3), 0.1% (wt/vol) gelatin] was combined with 10 µL of 10× dNTP mix (2 mM dGTP, 2 mM dATP, 10 mM dCTP, 10 mM dTTP), 30 pmoles each of a forward and reverse primer designed to amplify the DNA of interest. For the scFv genes we used: (AXL6AS4-PCRR 5'Phos G*T*C*G*ACTGAGGAGACGGTGACC); and (AXL6KunkPCRF2 AAGCTTTCCTATGAGCTGACACA-GCC), with asterisks demarcating basepairs joined by a phosphorothioate. Reactions utilized either 1, 10, or 20 fmoles of input DNA, (i.e., a separate reaction for each amount), with water added to a total volume of 88 µL. 10 µL of 5 mM MnCl$_2$ was then added and mixed well; the absence of any precipitate was verified. 2 µL of Taq DNA polymerase was added to bring the final volume to 100 µL. Reactions were cycled on a Biorad T100 Thermal Cycler for 30 cycles (94° C. 1 min., 55° C. 1 min., 72° C. 1 min). After PCR was complete, reaction cleanup was performed using the Qiagen QIAquick PCR Purification Kit according to the manufacturer's protocol. Product size was approximately 800 base pairs.

Example 3: T7 Treatment

To digest the strand with less than three phosphorothioates, 40 µl of PCR product purified using the Qiagen QIAquick PCR Purification Kit was incubated with 10 µl T7 exonuclease (10,000 units per ml) in 1×NEB buffer 4 at 25° C. for 1 hr in a BioRad T100 Thermal Cycler. The T7-treated product was purified using the Qiagen QIAquick PCR Purification Kit and eluted in 40 µl EB buffer per reaction.

These phosphorothioates provide protection of the initial double-stranded PCR product from the hydrolytic action of the 5' to 3' exonuclease T7 while the opposite, non-protected strand is hydrolyzed. We found that one or two phosphorothioates was not sufficient to prevent hydrolysis, but the addition of 3 or 4 phosphorothioates resulted in complete protection of the corresponding strand.

The phosphorothioates may provide an additional benefit in vivo by protecting any incompletely ligated heteroduplex product from degradation by cytosolic exonucleases in E. coli, preventing biased incorporation of mutations.

Conversion of Double-Stranded PCR Product to Single-Stranded DNA Variant.

Figure 2:
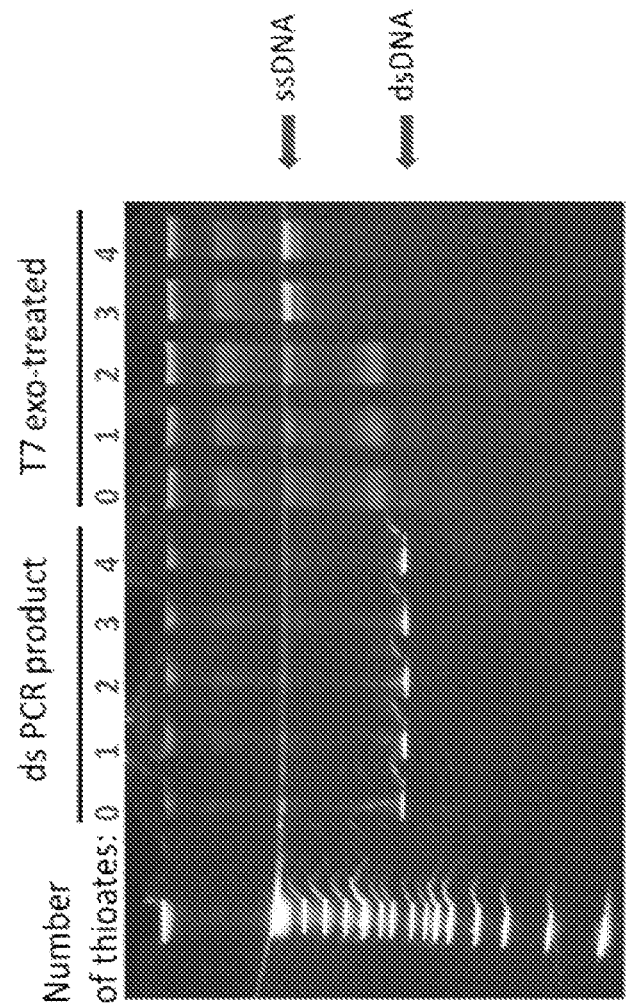
FIG. 2 is a native acrylamide gel stained with SYBR Gold showing the conversion of dsDNA error-prone PCR products to ssDNA molecules. The first lane contains a ladder. Untreated dsDNA error-prone PCR products are shown in the first five lanes after the ladder. T7 exonuclease was added to error-prone PCR products in the last 5 lanes. Error-prone PCR products were generated using an unmodified forward primer and a phosphorylated reverse primer that was either unmodified or modified with one, two, three, or four 5'-phosphorothiates, as labeled over each lane. As can be seen from this gel analysis, at least three 5' phosphorothiates are needed to protect a strand from the exonuclease activity of the T7 enzyme.

PCR products from amplification of an 800 base pair scFv gene under conditions that favor nucleotide misincorporation were treated either with or without T7 or lambda exonuclease for 1 hour at 25° C. Following treatment, the products were visualized on a native acrylamide gel stained with SYBR-Gold. The ssDNA product shows slower mobility than the corresponding dsDNA (FIG. 2). As expected, T7 exonuclease fully degrades the unprotected DNA if neither primer contains phosphorothioates. One or two phosphorothioate residues on the 5' end also does not provide sufficient protection from the hydrolytic action of the enzyme (FIG. 2). However, when one of the 5' ends has 3 or 4 phosphorothioates, the PCR product is fully converted to ssDNA (FIG. 2). Lambda exonuclease also converts the dsDNA to ssDNA, but the reaction is more efficient when the non-phosphorothioate primer is 5' phosphorylated.

Example 4: Heteroduplex Formation

To incorporate single-stranded products of error-prone PCR followed by T7 digestion into a DNA heteroduplex, 40 µl of T7 treated- and cleaned-up reaction was added to 13 µl of pAX143 ssDNA, 25 µl 10× TM (0.1 M MgCl$_2$, 0.5 M Tris, pH 7.5) buffer, and 172 µl dH$_2$0. pAX143 is a derivative of the phagemid, pAP-III$_6$ with a single-chain variable fragment antibody (scFv) fused to the bacteriophage M13 gpIII coat protein. The scFv in pAX143 contains stop codons and Sac II restriction sites in each of the CDRs so that non-recombinant clones are rendered non-functional. In reactions with synthetic oligonucleotides, 200 ng of oligonucleotide were added to 20 µg circular, single-stranded template. The annealing reaction was carried out by incubation at 90° C. for 2 min. followed by a gradual decline from 90° C. to 55° C. at −1° C. per minute in a BioRad T100 thermocycler. The annealed product was then combined with 10 µl of 10 mM ATP, 10 µl of 100 mM dNTP mix, 15 µl of 100 mM DTT, 0.5 µl (30 U) T4 DNA ligase and 3 µl (30 U) T7 DNA polymerase. The mixture is aliquoted equally into 5 PCR tubes and incubated overnight (16 hrs) at 20° C. in a BioRad T100 thermocycler.

The resultant DNA was desalted and purified using a Qiagen QIAquick DNA purification kit. This was accomplished by mixing the reaction with 1.0 ml of buffer QG (Qiagen QIAquick DNA purification kit). The samples were eluted by the addition of 35 µl of buffer EB (Qiagen QIAquick DNA purification kit) to each column. The eluants from 2 columns (70 µl final) were combined and 2 µl of the product was visualized on an agarose gel alongside 2 µl of ssDNA. Up to 3 bands were observed. The upper (and often most prevalent) band corresponds to stand displaced DNA, the middle (usually faint) band corresponds to nicked DNA (i.e., not properly extended and ligated), and the lower band represents the correctly extended and ligated product. The ssDNA will run lower than the correctly ligated band.

For standard cloning of the error-prone PCR product, the DNA was digested with HindIII and SalI and ligated into the pAPIII$_6$ vector for phage display.

Example 5: Transformation of CJ236 Strain

The CJ236 strain (Genotype: FΔ(HindIII)::cat(Tra$^+$ Pil$^+$ Cam$^R$)/ung-1 relA1 dut-1 thi-1 spoT1 mcrA) was purchased from New England Biolabs. This strain lacks functional dUTPase and uracil-N glycosylase, and is used for generating the uracilated, single-stranded DNA template. An aliquot (25 µl) of electrocompetent CJ236 cells was pipetted into a chilled 0.1 mm gap cuvette, and 1 µl of pAPIII6 plasmid DNA was added to the CJ236 cells in the cuvette. The cells were electroporated at 1.6 volts in a BioRad electroporator. Immediately after electroporation, 1 ml of SOC media was added and the media plus cells were transferred to a 14 ml Falcon-brand culture tube. The culture was incubated at 37° C. with shaking (~225 rpm) for 1 hour. At the end of the hour, 250 µl of the transformed cells are spread directly on a LB +CAM +AMP plate. The plates were incubated overnight at 37° C.

Example 6: Library Transformation

The TG1 E. coli strain (F' [traD36 proAB+ lacIq lacZΔM15]supE thi-1 Δ(lac-proAB) Δ(mcrB-hsdSM)5, (rK- mK-) was purchased from Lucigen. For transformation reactions 0.5 µl heteroduplex DNA or ligation product was mixed with 25 µl of TG1 electrocompetent cells (Lucigen) and added to 0.1 cm gap cuvette. The cells plus DNA were electroporated using a GenePulser set to 1.6 kV, (r1.60 on "set volts"), 200 ohms, 25 µF. Electroporated cells were mixed with 1 ml of Lucigen recovery and transferred to a 14 ml Falcon culture tube, then shaken at 37° C. After 1 hour, 2 µl of the culture was removed and diluted $10^{-2}$ into 198 µl of 2YT media and vortexed to mix. Then, using a clean pipet, 2 µl of the $10^{-2}$ dilution was further diluted into 198 µl of 2YT media for a $10^{-4}$ dilution. These $10^{-2}$ serial dilutions were repeated up to $10^{-14}$. 100 µl of each of the dilutions was plated by sterile spreader onto TYE-AMP-glucose plate and the plates were incubated overnight at 37° C.

Example 7: Kunkel Mutagenesis

The effect of ssDNA products with 5' phosphorthiate bonds on the efficiency of Kunkel mutagenesis, and in particular biased repair of the uracilated DNA strand in favor of the in vitro synthesized recombinant strand, was studied in E. coli. A synthetic oligonucleotide containing 4 phosphorothioates at the 5' end and was used in a standard Kunkel mutagenesis reaction in parallel with the same oligonucleotide lacking the phosphorothioates. The heteroduplex DNA product was transformed into E. coli TG1 cells that encode wild type versions of the enzymes required for removal of uracils in DNA and favor propagation of the recombinant, non-uracilated strand. Recombinants were generated from both the unmodified and modified oligonucleotides at rates of 44% and 50%, respectively (Table 1), indicating that phosphorothioate oligonucleotides can be used for Kunkel mutagenesis.

Figure 3:
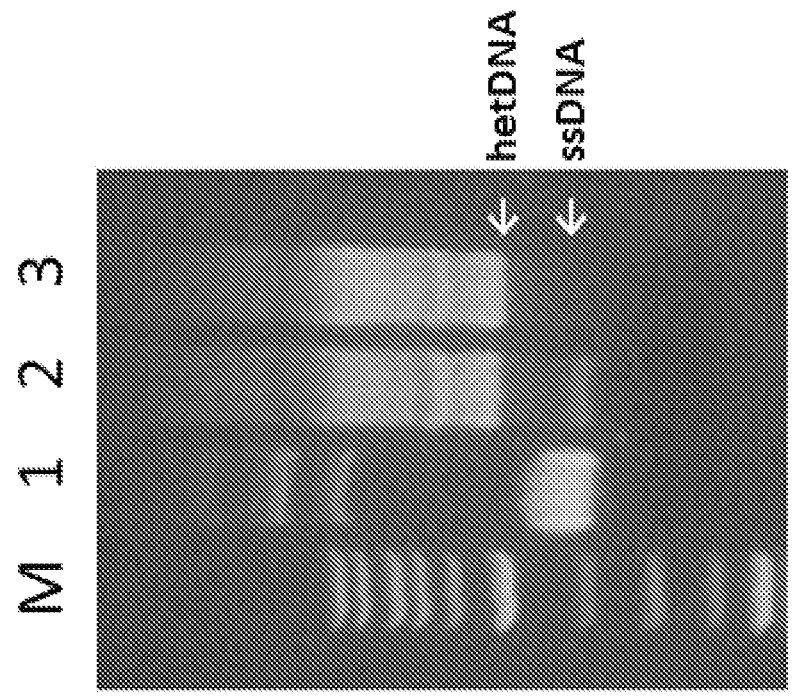
FIG. 3 is an agarose gel electrophoresis showing the conversion of ssDNA to heteroduplex DNA. ssDNA molecules were hybridized to uracilated, circular ssDNA molecules to form heteroduplexes. Lane M is 2 log DNA ladder (New England Biolabs). Lanes one, two and three are uracilated, circular ssDNA (pAX143) alone, heteroduplex formed with 3:1 ratio of ssDNA variants to uracilated circular ssDNA intermediaries, and heteroduplex formed with 10:1 ratio of ssDNA variants to uracilated circular ssDNA intermediaries, respectively. Y-axis labels indicate the bands of uracilated, circular ssDNA (pAX143) alone (ssDNA) and heteroduplex DNA (hetDNA).
Figure 4:
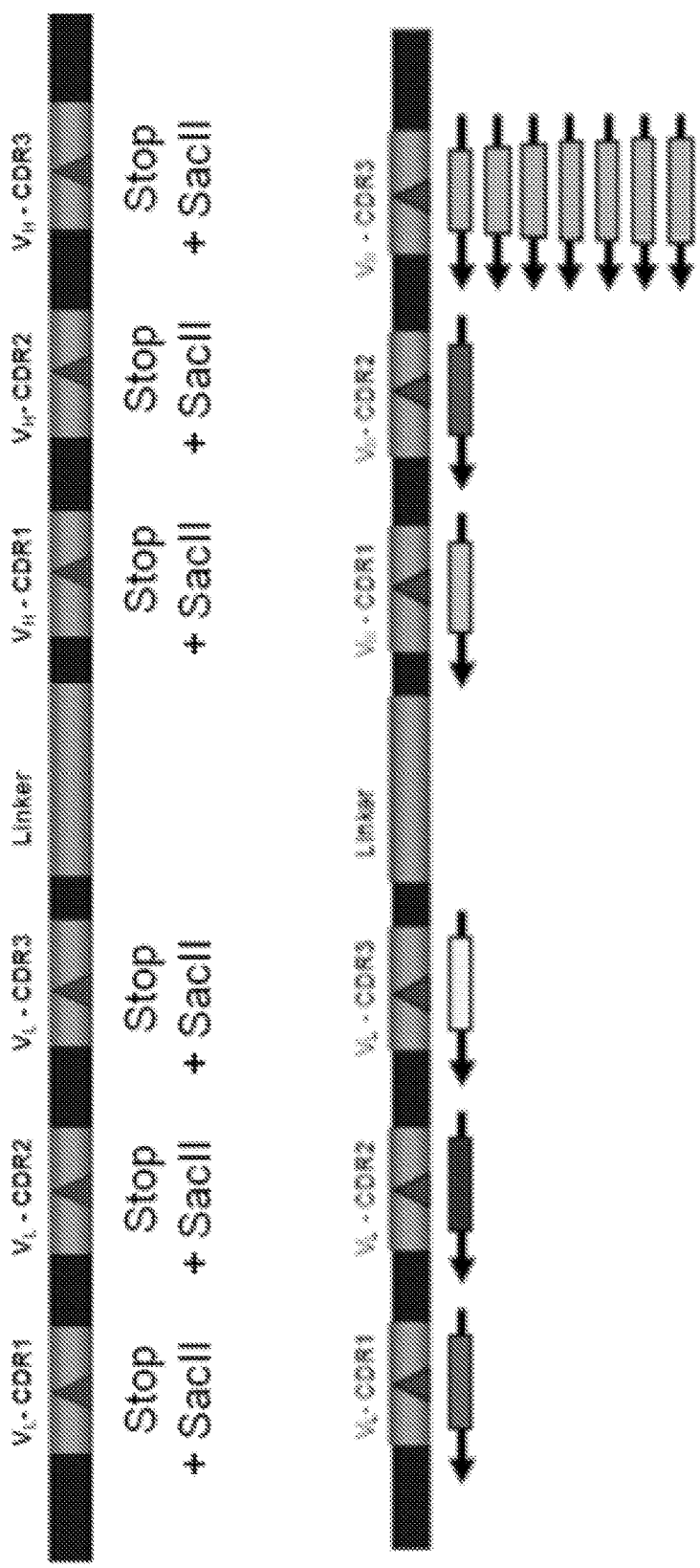
FIG. 4 is a pair of diagrams showing scFv constructs. The upper construct is representative of an ssDNA intermediary sequence. The lower construct is representative of a template DNA molecule.

The synthetic oligonucleotide was substituted for the ssDNA variant generated by T7 exonuclease treatment of an 800 base pair error-prone PCR fragment corresponding to a mutated scFv gene. Since the mutated ssDNA variant is 20 times larger than the oligonucleotide, the ratio of the ssDNA variant to the uracilated, circular, single-stranded template had to be optimized to achieve efficient production of a heteroduplex product (FIG. 3). Following electroporation of the dsDNA product into TG1 cells, individual clones were sent for sequencing to determine the number of recombinants. Recombinants were generated at a rate of 46%, which is comparable to the efficiencies observed with synthetic oligonucleotides. In addition to full recombinants, the ssDNA variant reaction also yielded partial recombinants, in which part of the ssDNA variant sequence was incorporated, at a frequency of 35% (9 of 26 recombinants; Table 1).

TABLE 1

Analysis of recombinants from Kunkel mutagenesis reactions

| Input DNA | Number of recombinants | Number of non-recombinants | Number of partial recombinants | % recombinants |
|---|---|---|---|---|
| Standard oligo | 7 | 9 | 0 | 43.75 |
| Phosphorothioated oligo | 8 | 8 | 0 | 50 |
| Phosphorothioated ssDNA variant | 12 | 5 | 9 | 46 |

Example 8: Generation of Diverse Libraries Using AXM Mutagenesis

To compare the present method to the conventional approach of generating affinity maturation libraries by error-prone PCR, the same scFv gene as above was amplified by error-prone PCR and sub-cloned into the phagemid vector using standard techniques. Following electroporation of the ligated product into TG1 cells, serial dilutions were plated onto solid media in order to get an estimate of the number of transformants. Individual clones were sequenced to determine the percentage of recombinants and mutation frequencies.

Among the transformants from the standard library, 75% were recombinant, and on average, each recombinant clone had 8 mutations, which is equal to a point mutation rate of approximately 1% (Table 2). A similar mutation rate of 1.5% was observed using the AXM mutagenesis approach (Table 2). Although the frequency of recombinants was slightly higher for the standard library than for the AXM mutagenesis library, the overall number of transformants was several orders of magnitude higher using the AXM mutagenesis approach ($2.8 \times 10^8$ versus $1 \times 10^5$, respectively). Based on these efficiencies, the overall library diversity from a single transformation using the AXM mutagenesis approach was approximately $10^8$ recombinant clones (Table 2). To achieve a similar size library using the standard approach would require 1000 transformations. This result shows that the present method allows efficient generation of libraries with $10^8$ recombinant clones from a single transformation. The conventional error-prone PCR and sub-cloning approach required 1000 transformations to yield a library of equivalent size.

TABLE 2

Comparison of library diversity using conventional approach and AXM mutagenesis approach

| Mutagenesis method | Number of transformants | % recombinants | Library diversity | Average number of mutations | Mutation rate of recombinants |
|---|---|---|---|---|---|
| Std Error-prone PCR | 1.00E+05 | 75 | 7.50E+04 | 8.3 | 1.1 |
| AXM mutagenesis | 2.80E+08 | 46.15 | 1.29E+08 | 11.7 | 1.5 |

Example 9: Methods of Determining the Efficiency of Mutagenesis

A blue/white screen was used to determine the efficiency of mutagenesis. pBluescript vector including a lacZ gene capable of expressing β-Galactosidase was used in these experiments. Control cells were transformed with pBluescript vectors having been hybridized to LacZ ssDNA variants having been amplified by standard PCR. These transformed cells were cultured in the presence of X-gal; 1480 of 1490 of these cells were blue (0.01% white colonies). Cells transformed with pBluescript vectors having been hybridized to LacZ ssDNA variants having been amplified by error prone PCR were separately cultured in the presence of X-gal. 525 of 627 cells were blue (19% white colonies). Additional cells were separately transformed with scFv templates having been amplified by error prone PCR. In each of two samples in which an scFv template was amplified by error prone PCR, hybridized to a vector, and cultured on X-gal, 100% of the colonies were white. A Kunkel efficiency for these cells of 21% was determined (Table 3).

TABLE 3

Blue/White Screen for Determining the Efficiency of Mutagenesis

| PCR | Template | Colonies (white) | Colonies (blue) | % White | Kunkel Efficiency (%) | Mutagenesis Frequency (per 100 bp) |
|---|---|---|---|---|---|---|
| Std PCR | pBluescript | 10 | 1480 | 0.01 | n/a | n/a |
| EP PCR | pBluescript | 102 | 525 | 19 | n/a | ⅛ |
| EP PCR | scFv 1 | 800+ | 0 | n/a | 21 | 2 |
| EP PCR | scFv 2 | 800+ | 0 | n/a | 21 | 2.7 |

Example 10: Mutagenesis of Immunoglobulin Heavy and Light Chains on Separate Vectors In one example of the present invention, a first sequence of interest encodes an immunoglobulin heavy chain and a second sequence of interest encodes an immunoglobulin light chain. Each is mutagenized according to the methods of the present invention to produce dsDNA variants, which are then converted to ssDNA variants and hybridized to ssDNA intermediaries to form heteroduplexes. Immunoglobulin light chain ssDNA variants will be hybridized to a first ssDNA intermediary, while immunoglobulin heavy chain ssDNA variants will be hybridized to a second, separate, ssDNA intermediary. The hybridized ssDNA variants will prime DNA extension using the ssDNA intermediary as a template molecule. The extension reaction will include a ligase. Afterward, the ssDNA intermediary will be degraded either before or after transformation into bacteria. Any or all steps may occur in a single reaction pool or in two or more separate reaction pools, e.g., including at least one for immunoglobulin light chain variants and another for immunoglobulin heavy chain variants. A single pool of bacteria are transformed with the produced immunoglobulin light chain vectors and the produced immunoglobulin heavy chain vectors. A subset of transformed cells are transformed with both one or more immunoglobulin light chain vectors and one or more immunoglobulin heavy chain vectors. In such instances, a heavy chain variant and a light chain variant may be co-expressed, allowing expressed heavy chain proteins and expressed light chain proteins to form an immunoglobulin complex, i.e., an antibody. Expression of the heavy chain variant and light chain variant may occur in a bacterial cell type into which the vectors are initially transformed or in a different cell type into which the vectors or vectors derived therefrom are subsequently transferred.

Example 11: Mutagenesis of Immunoglobulin Heavy and Light Chains on a Single Vector In one example of the present invention, a first sequence of interest encodes an immunoglobulin heavy chain and a second sequence of interest encodes an immunoglobulin light chain. The immunoglobulin heavy chain and immunoglobulin light chain sequences are cloned into a single vector. Each is mutagenized according to the methods of the present invention to produce dsDNA variants, which are then converted to ssDNA variants and hybridized to ssDNA intermediaries to form heteroduplexes, each ssDNA intermediary having at least one locus capable of hybridizing to an immunoglobulin heavy chain ssDNA variant and a separate locus capable of hybridizing to an immunoglobulin light chain ssDNA variant. The hybridized ssDNA variants will prime DNA extension using the ssDNA intermediary as a template molecule. The extension reaction will include a ligase. Afterward, the ssDNA intermediary will be degraded either before or after transformation into bacteria. A heavy chain variant and a light chain variant cloned into a single vector by a method of the present invention may be co-expressed, allowing expressed heavy chain proteins and expressed light chain proteins to form an immunoglobulin complex, i.e., an antibody. Expression of the heavy chain variant and light chain variant may occur in a bacterial cell type into which the vector was initially transformed or in a different cell type into which the vector or a vector derived therefrom was subsequently transferred.

Example 12: Use of Eco29kl Restriction Sites to Select for Resolved Vectors

In some instances of the present invention it is desirable to incorporate ssDNA variants corresponding to a plurality of distinct polynucleotide segments into a single resolved vector. In this example, the methods of the present invention are used to replace, in a single construct, each of 6 complementarity determining regions of a single chain antibody with the sequence of an ssDNA variant capable of hybridizing thereto. The single chain antibody includes a light chain variable domain ($V_L$) complementary determining region (CDR) 1 (together, $V_L$-CDR1), a $V_L$-CDR2, a $V_L$-CDR3, a linker, a heavy chain variable domain ($V_H$) CDR1 (together, $V_H$-CDR1), $V_H$-CDR2, and $V_H$-CDR3. The distance between any two adjacent CDRs may be, e.g., 30 to 40 base pairs.

ssDNA variants capable of hybridizing to each of the CDRs are generated based upon template sequences corresponding to each of the CDRs. The template sequences do not include SacII restriction sites or opal stop codons (FIG. 4). The ssDNA variants hybridize to uracilated ssDNA intermediaries having sequences to which the CDR ssDNA variants are capable of hybridizing, but further including a SacII restriction site and opal stop codon within the segment of each CDR to which the corresponding ssDNA variants are capable of hybridizing (FIG. 4). The ssDNA variants are hybridized to the ssDNA intermediaries and subsequently transferred to bacteria, wherein mismatched nucleotides are resolved. These bacteria express the Eco29kl restriction enzyme, capable of degrading a vector including a complete SacII restriction site. Accordingly, if any one of the 6 CDRs of the intermediary strand does not hybridize to an ssDNA variant, or if any one of the 6 CDRs hybridizes to a corresponding ssDNA variant but does not resolve in favor of the ssDNA intermediary strand rather than the hybridized ssDNA variant at the SacII restriction site, the resulting vector includes one or more SacII restriction sites. Such vectors are degraded in the bacteria expressing Eco29kl. By eliminating those vectors that are not resolved in favor of an ssDNA variant at each of the 6 CDRs, the efficiency of identifying constructs modified at all 6 CDRs is increased. Similarly, presence of any opal mutation disrupts expression of the single chain antibody, or variant thereof, encoded by the resolved vector.

Example 14: Use of Eco29kl Restriction to Improve the Percentage of Recombinants To demonstrate the increased frequency with which recombinants are identified when using the Eco29kl restriction method described herein, several conditions were tested. In a first condition, ssDNA variants were generated from scFv templates (scFv1 or scFv2). The ssDNA variants do not include a SacII restriction site. The ssDNA variants were hybridized to ssDNA intermediaries that include SacII restriction sites within the segment of the ssDNA intermediaries to which the ssDNA variants were capable of hybridizing. Transformation into TG1 cells expressing Eco29kl results in resolution of mismatch nucleotides and degradation of vectors that include a SacII restriction site. In a second condition, an scFv 2 template was used to generate ssDNA variants, and the ssDNA variants were hybridized to an ssDNA intermediary that did not include a SacII restriction site. In this second condition, transformation into TG1 cells expressing Eco29kl does not result in the degradation of vectors that include a SacII restriction site. Because degradation of vectors including a SacII restriction site selectively degrades vectors that did not complete recombination, the percentage of recombinants is increased. This effect is compared in cells that do not express Eco29kl (TG1 cells), with or without in vitro treatment with SacII.

The results below show that restriction of non-recombinant vectors in TG1 cells expressing Eco29kl produces a higher percentage of recombinants than is observed with TG1 cells that do not express Eco29kl.

TABLE 4

| | | Percentage recombinants | | |
|---|---|---|---|---|
| Template | ssDNA intermediary restriction site | No restriction | In vitro restriction (SacII) | In vivo restriction (Eco29kI) |
| scFv1 | SacII | 40% | 75% | 89% |
| scFv2 | SacII | 31% | 87% | >99% |
| scFv2 | (none) | 30% | No data | 29% |

OTHER EMBODIMENTS

All publications, patent applications, and patents mentioned in this specification are herein incorporated by reference.

While the invention has been described in connection with the specific embodiments, it will be understood that it is capable of further modifications. Therefore, this application is intended to cover any variations, uses, or adaptations of the invention that follow, in general, the principles of the invention, including departures from the present disclosure that come within known or customary practice within the art.

What is claimed is:

1. A method of selectively degrading a non-mutagenized nucleic acid, the method comprising:
   (a) providing a first nucleic acid comprising at least one segment having a restriction site;
   (b) providing at least one second nucleic acid having at least one segment that does not comprise said restriction site and is capable of hybridizing to at least a segment of said first nucleic acid having said restriction site;
   (c) hybridizing said at least one second nucleic acid to said first nucleic acid, generating heteroduplex DNA;
   (d) extending and ligating said heteroduplex DNA to form a ligated heteroduplex product;
   (e) transforming said ligated heteroduplex product into a cell expressing a restriction enzyme capable of cleaving said restriction site;
   (f) incubating said cell in a manner sufficient to allow cleavage of said ligated heteroduplex product by said restriction enzyme expressed by said cell, thereby generating a product that does not include a restriction site cleaved by said restriction enzyme;
   (g) determining whether said cell comprises said product; and
   (h) isolating said product from said cell.

2. The method of claim 1, wherein said restriction enzyme is Eco29kI.

3. The method of claim 1, wherein said product encodes an immunoglobulin light chain and/or an immunoglobulin heavy chain, wherein said immunoglobulin light chain and/or said immunoglobulin heavy chain is encoded by at least a portion of said first nucleic acid and at least a portion of said at least one second nucleic acid.

4. The method of claim 1, wherein said first nucleic acid is an ssDNA intermediary and said at least one second nucleic acid is an ssDNA variant.

5. The method of claim 1, wherein said at least one segment of the first nucleic acid comprises a sequence encoding a vector.

6. The method of claim 1, wherein said at least one segment of the second nucleic acid comprises a sequence encoding at least one of a scFv light chain variable region, a scFv heavy chain variable region, a scFv linker region, an IgG heavy chain constant region, an IgG light chain constant region, a gpIII protein, and any combination thereof.

7. The method of claim 1, wherein said product comprises a sequence that encodes:
   i) a full-length immunoglobulin Fv light chain, wherein said full-length immunoglobulin Fv light chain is encoded by at least a portion of said first nucleic acid and at least a portion of said second nucleic acid; or
   ii) a full-length immunoglobulin Fv heavy chain, wherein said full-length immunoglobulin Fv heavy chain is encoded by at least a portion of said first nucleic acid and at least a portion of said at least one second nucleic acid; or
   iii) a full-length immunoglobulin Fv light chain and a full-length immunoglobulin Fv heavy chain, one or more of said full-length immunoglobulin Fv light chain and said full-length immunoglobulin Fv heavy chain being encoded by at least a portion of said first nucleic acid and at least portion of said at least one second nucleic acid.

* * * * *

UNITED STATES PATENT AND TRADEMARK OFFICE
CERTIFICATE OF CORRECTION

PATENT NO. : 10,301,617 B2
APPLICATION NO. : 15/476304
DATED : May 28, 2019
INVENTOR(S) : Michael Weiner et al.

It is certified that error appears in the above-identified patent and that said Letters Patent is hereby corrected as shown below:

In the Claims

Column 31, in Claim 2, Line 36, replace "Eco29kl" with --Eco29kI--.

Signed and Sealed this
Twenty-fourth Day of December, 2019

Andrei Iancu
*Director of the United States Patent and Trademark Office*

SEQUENCE LISTING

<160> NUMBER OF SEQ ID NOS: 2

<210> SEQ ID NO 1
<211> LENGTH: 22
<212> TYPE: DNA
<213> ORGANISM: Artificial Sequence
<220> FEATURE:
<223> OTHER INFORMATION: Synthetic Construct

<400> SEQUENCE: 1
gtcgactgag gagacggtga cc 22

<210> SEQ ID NO 2
<211> LENGTH: 26
<212> TYPE: DNA
<213> ORGANISM: Artificial Sequence

```
-continued

<220> FEATURE:
<223> OTHER INFORMATION: Synthetic Construct

<400> SEQUENCE: 2
aagctttcct atgagctgac acagcc                                              26
```